(12) United States Patent
Alyagon et al.

(10) Patent No.: US 11,400,289 B2
(45) Date of Patent: Aug. 2, 2022

(54) APPARATUS AND METHODS FOR PREDICTING THERAPY OUTCOME

(71) Applicants: BRAINSWAY LTD, Jerusalem (IL); ELMINDA LTD., Herzliya (IL); B. G. NEGEV TECHNOLOGIES AND APPLICATIONS LTD., Beer Sheva (IL)

(72) Inventors: Uri Alyagon, Omer (IL); Abraham Zangen, Jerusalem (IL); Gaby S. Pell, Jerusalem (IL); Yiftach Roth, Rechelim (IL); Ronen Segal, Jerusalem (IL); Amir Geva, Tel Aviv (IL); Ziv Peremen, Tel Aviv (IL); Boaz Sadeh, Rehovot (IL); Revital Shani-Hershkovich, Mazkeret Batya (IL); Dror Haor, Doar Na Emek Soreq (IL)

(73) Assignees: BRAINSWAY LTD., Jerusalem (IL); ELMINDA LTD., Herzliya (IL); B. G. NEGEV TECHNOLOGIES AND APPLICATIONS LTD., Beer Sheva (IL)

(*) Notice: Subject to any disclaimer, the term of this patent is extended or adjusted under 35 U.S.C. 154(b) by 8 days.

(21) Appl. No.: 16/344,499

(22) PCT Filed: Oct. 25, 2017

(86) PCT No.: PCT/IL2017/051163
§ 371 (c)(1),
(2) Date: Apr. 24, 2019

(87) PCT Pub. No.: WO2018/078619
PCT Pub. Date: May 3, 2018

(65) Prior Publication Data
US 2019/0247654 A1      Aug. 15, 2019

Related U.S. Application Data

(60) Provisional application No. 62/412,598, filed on Oct. 25, 2016.

(51) Int. Cl.
*A61N 1/36*      (2006.01)
*A61N 2/00*      (2006.01)
(Continued)

(52) U.S. Cl.
CPC ........ *A61N 1/36025* (2013.01); *A61B 5/0006* (2013.01); *A61B 5/165* (2013.01);
(Continued)

(58) Field of Classification Search
CPC ...... A61N 1/36025; A61N 2/02; A61N 2/006; A61B 5/4076; A61B 5/168;
(Continued)

(56) References Cited

U.S. PATENT DOCUMENTS

2005/0216071 A1* 9/2005 Devlin ............... A61N 1/36082
607/48
2011/0004115 A1   1/2011 Shahaf et al.
(Continued)

FOREIGN PATENT DOCUMENTS

WO    2006089181      8/2006
WO    2011086563 A2   7/2011
(Continued)

OTHER PUBLICATIONS

International Search Report and Written Opinion issued in corresponding International Patent Application No. PCT/IL2017/051163 dated Jan. 8, 2018.
(Continued)

*Primary Examiner* — Unsu Jung
*Assistant Examiner* — Natasha Patel
(74) *Attorney, Agent, or Firm* — Troutman Pepper Hamilton Sanders LLP

(57) ABSTRACT

Apparatus and methods are described for use with electrophysiological signal detecting electrodes, and a transcranial magnetic stimulation device. A computer processor drives the transcranial stimulation device to apply one or more pulses of transcranial magnetic stimulation to a subject. Within a given time period of applying one of the one or more pulses of transcranial magnetic stimulation to the subject, the computer processor detects an electrophysiological signal of the subject, using the electrophysiological signal detecting electrodes. At least partially in response thereto, the computer processor predicts an outcome of treating the subject for a neuropsychiatric condition, using a given therapy, and generates an output on an output device in response to the predicted outcome. Other applications are also described.

21 Claims, 16 Drawing Sheets

(51) Int. Cl.
  *A61N 2/02* (2006.01)
  *A61B 5/00* (2006.01)
  *A61B 5/16* (2006.01)
  *A61B 5/30* (2021.01)
  *A61B 5/291* (2021.01)
  *A61B 5/369* (2021.01)
  *A61B 5/377* (2021.01)

(52) U.S. Cl.
  CPC ............ *A61B 5/168* (2013.01); *A61B 5/291* (2021.01); *A61B 5/30* (2021.01); *A61B 5/369* (2021.01); *A61B 5/377* (2021.01); *A61B 5/4076* (2013.01); *A61B 5/7275* (2013.01); *A61N 2/006* (2013.01); *A61N 2/02* (2013.01)

(58) Field of Classification Search
  CPC ... A61B 5/04004; A61B 5/0476; A61B 5/165; A61B 5/7275; A61B 5/0006; A61B 5/0478; A61B 5/0484; G16H 50/30
  See application file for complete search history.

(56) References Cited

U.S. PATENT DOCUMENTS

| | | |
|---|---|---|
| 2011/0004412 A1 | 1/2011 | Shahaf et al. |
| 2011/0224571 A1 | 9/2011 | Alvaro et al. |
| 2012/0203130 A1 | 8/2012 | Bernhard |
| 2012/0296569 A1 | 11/2012 | Shahaf et al. |
| 2013/0080127 A1 | 3/2013 | Shahaf et al. |
| 2013/0178692 A1 | 7/2013 | Zangen et al. |
| 2013/0338424 A1 | 12/2013 | Pascual-Leone |
| 2014/0135886 A1* | 5/2014 | Cook .................. A61N 1/0456 607/136 |
| 2014/0163328 A1* | 6/2014 | Geva .................. G16H 50/70 600/300 |
| 2014/0228702 A1 | 8/2014 | Shahaf et al. |
| 2014/0235926 A1 | 8/2014 | Zangen et al. |
| 2014/0235927 A1 | 8/2014 | Zangen et al. |
| 2014/0235928 A1 | 8/2014 | Zangen et al. |
| 2014/0249352 A1 | 9/2014 | Zangen et al. |
| 2015/0305685 A1 | 10/2015 | Shahaf et al. |
| 2016/0008619 A1 | 1/2016 | Pell et al. |
| 2016/0038049 A1 | 2/2016 | Geva et al. |
| 2016/0059027 A1 | 3/2016 | Zangen et al. |
| 2016/0206895 A1 | 7/2016 | Zangen et al. |
| 2016/0206896 A1 | 7/2016 | Zangen et al. |
| 2016/0213276 A1 | 7/2016 | Gadot et al. |
| 2017/0216595 A1 | 8/2017 | Geva et al. |
| 2017/0291036 A1 | 10/2017 | Pell et al. |
| 2017/0296087 A1 | 10/2017 | Gadot et al. |
| 2018/0064952 A1 | 3/2018 | Zangen et al. |
| 2018/0310854 A1 | 11/2018 | Geva et al. |
| 2019/0053726 A1 | 2/2019 | Geva et al. |

FOREIGN PATENT DOCUMENTS

| | | |
|---|---|---|
| WO | 2013152354 | 10/2013 |
| WO | 2014140432 | 9/2014 |

OTHER PUBLICATIONS

European Search Report dated May 18, 2020 issued in connection with European Application No. 17794429.5.

Communication pursuant to Article 94(3) EPC dated Mar. 11, 2021 in connection with European Application No. 17794429.5.

\* cited by examiner

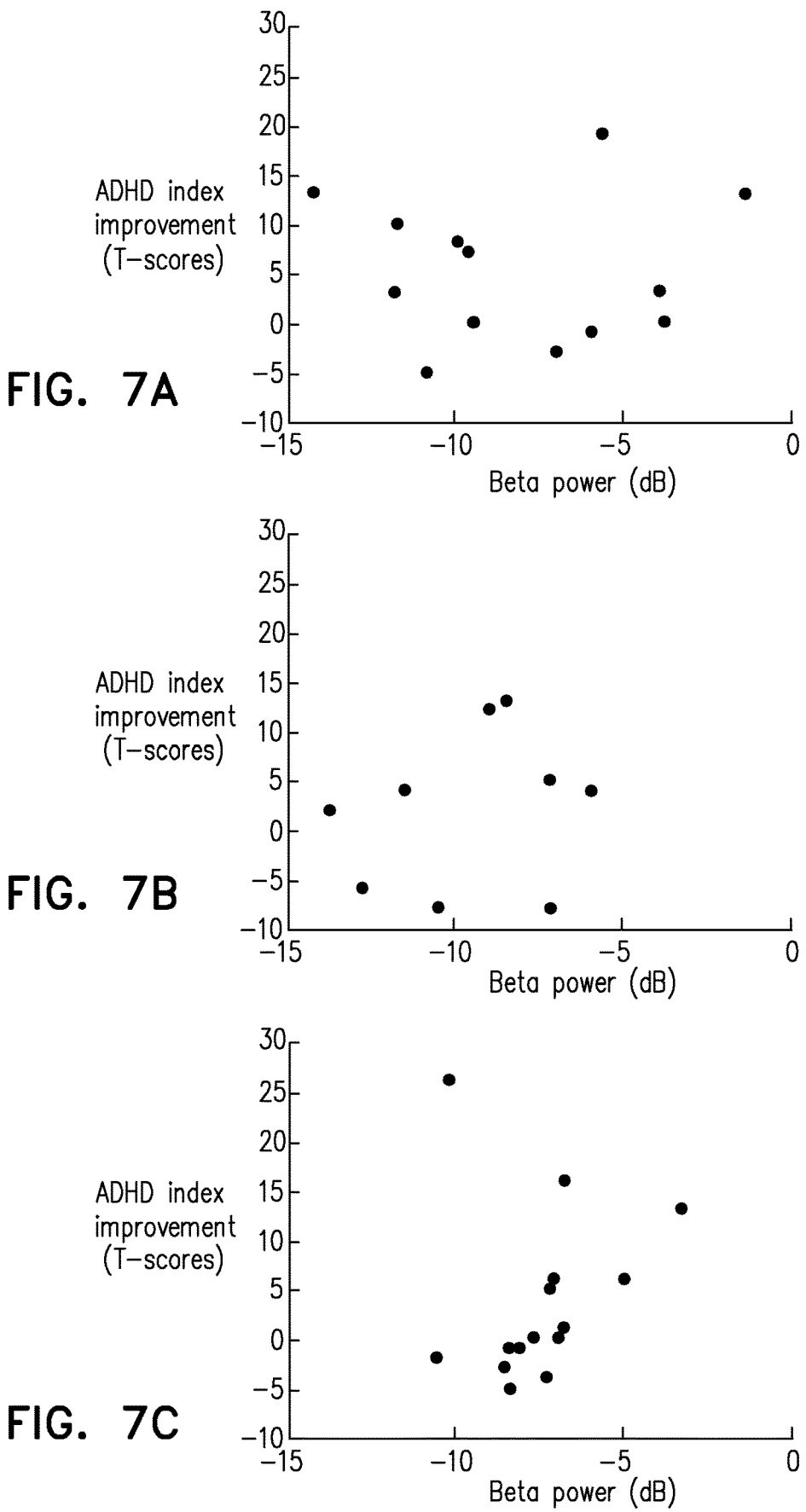

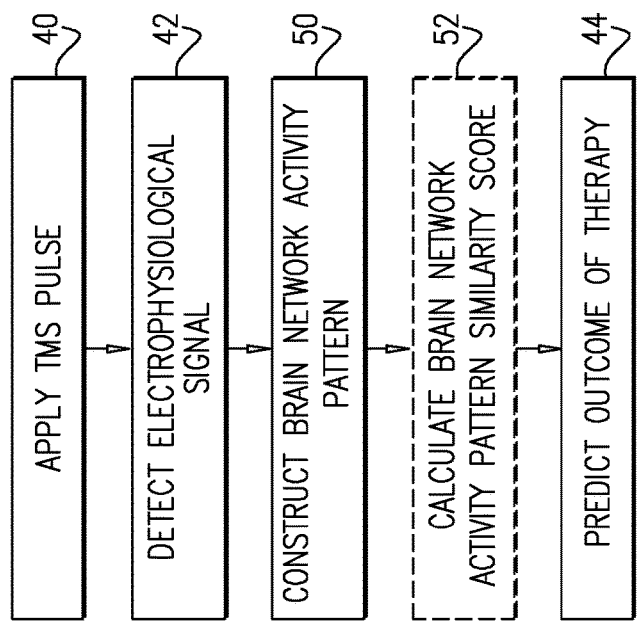
FIG. 15C
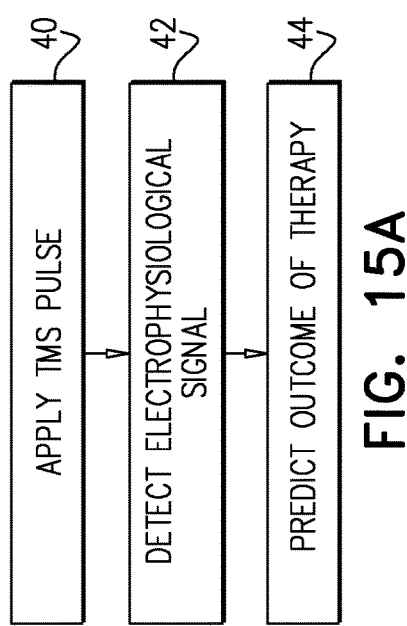
FIG. 15A
FIG. 15B

APPARATUS AND METHODS FOR PREDICTING THERAPY OUTCOME

CROSS-REFERENCE TO RELATED APPLICATIONS

The present application is the US national stage application of PCT/IL2017/051163, filed Oct. 25, 2017, which published as PCT Publication WO 2018/078619 to Alyagon, and which claims priority from U.S. Provisional Patent Application 62/412,598 to Alyagon, filed Oct. 25, 2016, entitled "Predicting therapy outcome," both of which are incorporated herein by reference.

FIELD OF EMBODIMENTS OF THE INVENTION

Some applications of the present invention relate to apparatus and methods for use with transcranial magnetic stimulation, and more particularly, to apparatus and methods for predicting the outcome of treatment of a condition using transcranial magnetic stimulation.

BACKGROUND

Transcranial magnetic stimulation (TMS) is widely used as a research tool to study aspects of the human brain and has recently been used as a tool in therapeutic neuropsychiatry. Biological tissue is stimulated using magnetic fields produced by passing electrical currents through electrically conductive materials positioned adjacent to the tissue. The magnetic fields cause electric conduction in brain cells, and, as a consequence, generation of action potentials.

The magnetic stimulation is delivered or generated by a coil, positioned on the patient's scalp, inducing nerve stimulation within the brain. Deep transcranial magnetic stimulation is described as being used in the treatment of depression and other neuropsychiatric disorders such as autism, post-traumatic stress disorder (PTSD), addictive behaviors (including smoking, eating disorders and drug addiction), schizophrenia, Parkinson's disease, and others. For example, a device for performing deep transcranial magnetic stimulation is described in International Publication Number WO 02/32504, which is incorporated herein by reference. The device described therein includes a base and an extension portion, the base having individual windings for individual paths of current flow, and the extension portion designed so as to minimize unwanted stimulation of other regions of the brain.

Reduced excitability of the right prefrontal cortex has been implicated in attention deficit/hyperactivity disorder (ADHD). Despite its high prevalence, available treatments for ADHD are not tolerable by many patients.

SUMMARY OF EMBODIMENTS

In accordance with some applications of the present invention, one or more pulses of transcranial magnetic stimulation (e.g., one or more trains of transcranial magnetic stimulation) are applied to a subject. For example, the subject may be a subject suffering from ADHD. Within a given time period of applying one of the one or more pulses of the transcranial magnetic stimulation to the subject, an electrophysiological signal (typically, an electroencephalography (EEG) signal) of the subject is detected. At least partially in response thereto, an outcome of treating the subject for a neuropsychiatric condition, using a given therapy is predicted, typically by means of a computer processor.

For some applications of the present invention, an electroencephalography (EEG) signal of the subject is detected. The power of a given frequency band within the detected EEG signal is calculated. For example, the power of a low gamma frequency band (e.g., a band from approximately 30 Hz to approximately 40 Hz) may be calculated. For some applications, the low gamma frequency band is normalized by being divided by the power of a different frequency band, such as an alpha frequency band (e.g., a band from approximately 8 Hz to approximately 15 Hz). At least partially based upon the power of the given frequency band, the outcome of treating the subject for a neuropsychiatric condition, using a given therapy is predicted.

For some applications, activity-related features are identified in the EEG signal, and a brain network activity (BNA) pattern is constructed based on those features. The brain network activity pattern typically includes a plurality of nodes, each representing a feature of the activity-related features, and a connectivity weight assigned to each pair of nodes.

For some applications, the pulses of transcranial magnetic stimulation are transmitted to the EEG system (or to a processor that receives and processes the EEG signal), and are used for identifying evoke responses in the brain. For some applications, the evoke responses are used for identifying activity-related features, and for constructing a brain network activity pattern.

For some applications, the nodes of the brain network activity pattern represent clusters of vectors of data characteristics. According to some applications of the invention, each vector of data characteristics of each cluster corresponds to data obtained from a different subject. Alternatively, all vectors of data characteristics correspond to data obtained from the same subject but in response to a separate transcranial magnetic stimulation stimulus.

According to some applications of the invention, a connectivity weight comprises a weight index calculated based on at least one cluster property selected from the group consisting of: (i) a number of vectors in a corresponding pair of clusters; (ii) a variability among numbers of vectors in the corresponding pair of clusters; (iii) a width of time windows associated with each cluster of the corresponding pair of clusters; (iv) a latency difference separating the corresponding pair of clusters, wherein the latency is with respect to time at which the transcranial magnetic stimulation pulse was applied; (v) amplitude of a signal associated with the corresponding pair of clusters; (vi) frequency of a signal associated with the corresponding pair of clusters; and (vii) the width of a spatial window defining the clusters.

There is therefore provided, in accordance with some applications of the present invention, apparatus for use with electrophysiological signal detecting electrodes, and a transcranial magnetic stimulation device, the apparatus including:

an output device; and
a computer processor configured to:
   drive the transcranial stimulation device to apply one or more pulses of transcranial magnetic stimulation to a subject;
   within a given time period of applying one of the one or more pulses of transcranial magnetic stimulation to the subject, detect an electrophysiological signal of the subject, using the electrophysiological signal detecting electrodes;

at least partially in response thereto, predict an outcome of treating the subject for a neuropsychiatric condition, using a given therapy; and generate an output on the output device in response to the predicted outcome.

In some applications, the computer processor is configured to predict the outcome of treating the subject for the neuropsychiatric condition, using the given therapy, by predicting an outcome of treating the subject for depression using transcranial magnetic stimulation.

In some applications, the computer processor is configured to predict the outcome of treating the subject for the neuropsychiatric condition, using the given therapy, by predicting an outcome of treating the subject for major depressive disorder using transcranial magnetic stimulation.

In some applications, the computer processor is configured to predict the outcome of treating the subject for the neuropsychiatric condition, using the given therapy, by predicting an outcome of treating the subject for ADHD using transcranial magnetic stimulation.

In some applications, the computer processor is configured to detect the electrophysiological signal of the subject by detecting an electroencephalography signal of the subject within the given time period of applying one of the one or more pulses of transcranial magnetic stimulation to the subject.

In some applications, the computer processor is configured to predict the outcome of treating the subject for the neuropsychiatric condition using the given therapy by predicting a response time of the subject to being treated with the given therapy.

In some applications, the computer processor is configured to predict the outcome of treating the subject for the neuropsychiatric condition using the given therapy by predicting a rate of improvement in the subject's neuropsychiatric condition, in response to being treated with the given therapy.

In some applications:
the computer processor is further configured to detect an electroencephalography (EEG) signal of the subject while the subject performs a task, and
the computer processor is configured to predict the outcome of treating the subject for the neuropsychiatric condition using the given therapy, based upon the electrophysiological signal of the subject and a component of the EEG signal of the subject that was detected while the subject performed the task.

In some applications, the computer processor is configured to drive the transcranial stimulation device to apply the one or more pulses of transcranial magnetic stimulation to the subject by driving the transcranial stimulation device to apply one or more trains of transcranial magnetic stimulation to the subject.

In some applications, the computer processor is configured to detect the electrophysiological signal of the subject by detecting the electrophysiological signal of the subject, while one of the one or more trains of transcranial magnetic stimulation is being applied to the subject.

In some applications, the computer processor is configured to detect the electrophysiological signal of the subject by detecting the electrophysiological signal of the subject, between trains of transcranial magnetic stimulation being applied to the subject.

In some applications, the computer processor is further configured to construct a brain network activity pattern based on the electrophysiological signal, and the computer processor is configured to predict the outcome of treating the subject for the neuropsychiatric condition using the given therapy based on the brain network activity pattern.

In some applications, the computer processor is further configured to calculate a brain network activity pattern similarity score, by comparing the brain network activity pattern to a group brain network activity pattern that is based upon electrophysiological signals acquired from a group of subjects, and the computer processor is configured to predict the outcome of treating the subject for the neuropsychiatric condition using the given therapy based on the brain network activity pattern similarity score.

In some applications, the computer processor is configured to construct the brain network activity pattern by constructing a brain network activity pattern that includes:
a plurality of nodes, each representing a comparison of features and relations among features in the electrophysiological signal to features and relations among features of reference neurophysiological data; and
connectivity weights assigned to respective pairs of nodes.

In some applications, the computer processor is configured to construct the brain network activity pattern by constructing a brain network activity pattern using electrophysiological signals acquired from a group of subjects as the reference neurophysiological data.

In some applications, the computer processor is configured to construct the brain network activity pattern by constructing a brain network activity pattern using, as the reference neurophysiological data, electrophysiological signals acquired from a group of subjects, each applied with an initial pulse of transcranial magnetic stimulation.

In some applications, the computer processor is configured to construct the brain network activity pattern by constructing a brain network activity pattern in which each node represents a cluster of vectors of data characteristics, and the connectivity weights of each one of the respective nodes represents at least one cluster property describing a pair of clusters represented by said the respective pair of nodes.

In some applications, the computer processor is configured to construct the brain network activity pattern by constructing a brain network activity pattern in which the at least one cluster property includes a latency difference separating the pair of clusters.

In some applications, the computer processor is further configured to calculate a power of a given frequency band within the detected electrophysiological signal, and the computer processor is configured to predict the outcome of treating the subject for the neuropsychiatric condition using the given therapy at least partially in response to the power of the given frequency band.

In some applications:
the computer processor is further configured to calculate powers of one or more additional frequency bands within the detected electrophysiological signal, and
the computer processor is configured to predict the outcome of treating the subject for the neuropsychiatric condition using the given therapy, based upon a combination of the power of the given frequency band and the powers of the one or more additional frequency bands.

In some applications, the computer processor is configured to predict the outcome of treating the subject for the neuropsychiatric condition using the given therapy, based upon a ratio of the power of the given frequency band and the power of one of the one or more additional frequency bands.

In some applications, the computer processor is configured to detect the electrophysiological signal of the subject by detecting an electroencephalography signal of the subject within the given time period of applying one of the one or more pulses of transcranial magnetic stimulation to the subject.

In some applications, the computer processor is configured to calculate the power of the given frequency band within the detected electrophysiological signal by calculating a power of a low gamma band within the detected electroencephalography signal.

In some applications:
the computer processor is further configured to calculate a power of an alpha band within the detected electroencephalography signal, and
the computer processor is configured to predict the outcome of treating the subject for the neuropsychiatric condition using the given therapy, based upon a combination of the power of the low gamma band within the detected electroencephalography signal and the power of the alpha band within the detected electroencephalography signal.

In some applications, the computer processor is configured to predict the outcome of treating the subject for the neuropsychiatric condition using the given therapy, based upon a ratio of the power of the low gamma band within the detected electroencephalography signal and the power of the alpha band within the detected electroencephalography signal.

There is further provided, in accordance with some applications of the present invention, a computer software product, for use with an output device, electrophysiological signal detecting electrodes, and a transcranial magnetic stimulation device, the computer software product including a non-transitory computer-readable medium in which program instructions are stored, which instructions, when read by a computer cause the computer to perform the steps of:
driving the transcranial stimulation device to apply one or more pulses of transcranial magnetic stimulation to a subject;
within a given time period of applying one of the one or more pulses of transcranial magnetic stimulation to the subject, detecting an electrophysiological signal of the subject, using the electrophysiological signal detecting electrodes;
at least partially in response thereto, predicting an outcome of treating the subject for a neuropsychiatric condition, using a given therapy; and
generating an output on the output device in response to the predicted outcome.

There is further provided, in accordance with some applications of the present invention, a method including:
applying one or more pulses of transcranial magnetic stimulation to a subject;
within a given time period of applying one of the one or more pulses of transcranial magnetic stimulation to the subject, detecting an electrophysiological signal of the subject;
at least partially in response to the detected electrophysiological signal, predicting an outcome of treating the subject for a neuropsychiatric condition, using a given therapy.

The present invention will be more fully understood from the following detailed description of embodiments thereof, taken together with the drawings, in which:

BRIEF DESCRIPTION OF THE DRAWINGS

FIGS. 7A, 7B, and 7C are graphs showing the relationship between improvements to T-scores of ADHD patients, and the power of the beta frequency band of an intra-treatment EEG that was recorded on the first day of a treatment, for patients that were treated using, respectively, a sham coil (FIG. 7A), a figure-eight coil (FIG. 7B), and a dTMS coil (FIG. 7C);

FIGS. 15A, 15B, and 15C are flowcharts showing steps that are performed by a computer processor, in accordance with some applications of the present invention.

DETAILED DESCRIPTION OF EMBODIMENTS

Figure 1:
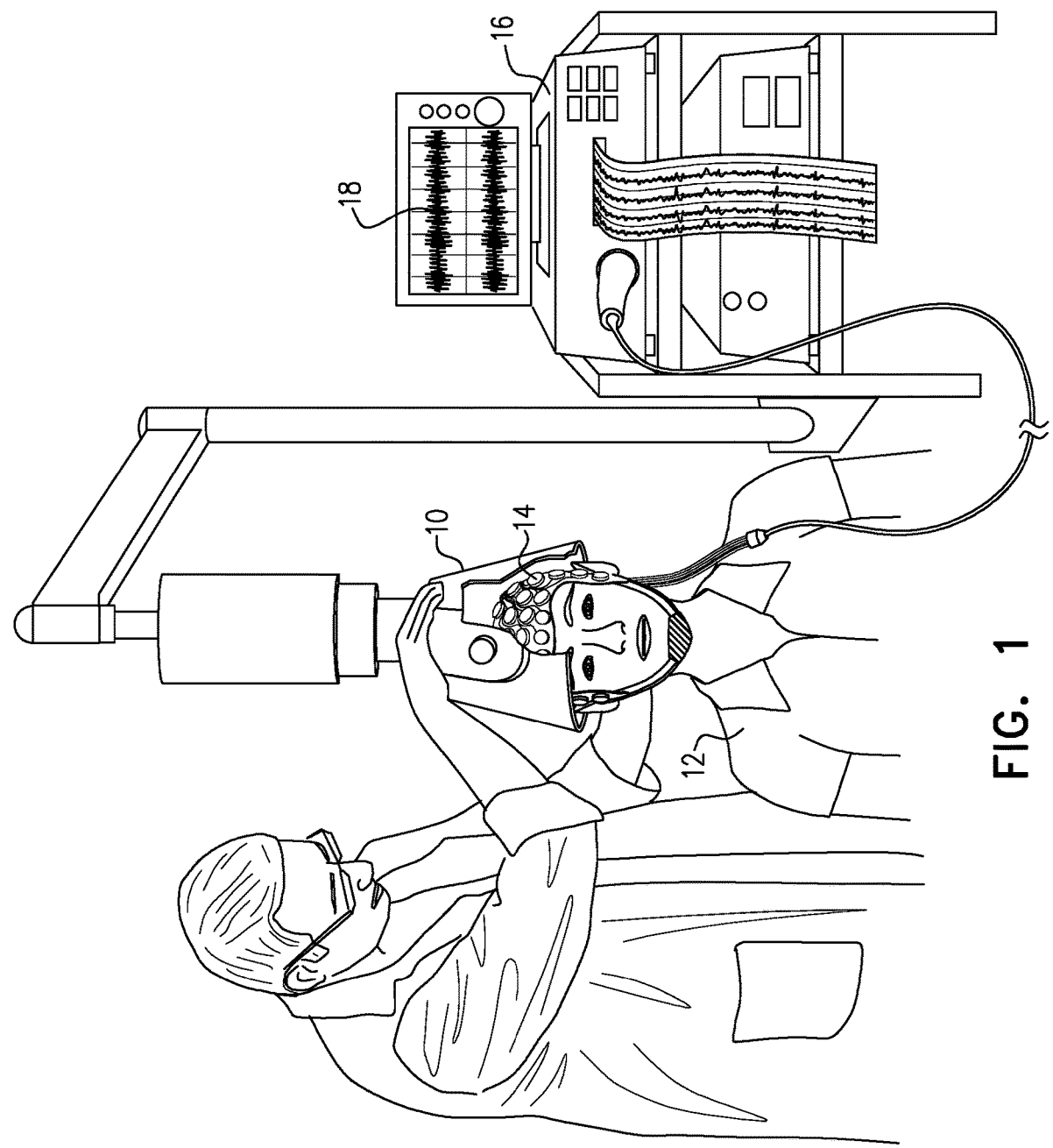
FIG. 1 is a schematic illustration of a transcranial magnetic stimulation (TMS) device applying TMS to a subject, while an electrophysiological signal of the subject, such as an electroencephalography (EEG) signal of the subject, is detected using electrodes, in accordance with some applications of the present invention.

Reference is now made to FIG. 1, which is a schematic illustration of a transcranial magnetic stimulation (TMS) device 10 applying TMS to a subject 12, while an electrophysiological signal of the subject, e.g., an electroencephalography (EEG) signal of the subject, is detected using electrodes 14, in accordance with some applications of the present invention. Typically, the TMS device and the electrodes are operatively coupled to one or more computer processors 16. Further typically, a user inputs data into the computer processor, and/or receives data from computer processor via one or more user interface devices. For example, as shown in FIG. 1, the computer processor may generate an output to the user via an output device, such as monitor 18.

In accordance with some applications of the present invention, one or more pulses of transcranial magnetic stimulation (e.g., a train of pulses that includes a plurality of pulses) are applied to a subject. For example, the subject may be a subject suffering from attention deficit hyperactivity disorder (ADHD). Within a given time period of having applied one of the one or more pulses of transcranial magnetic stimulation to the subject, an electrophysiological signal (typically, an electroencephalography (EEG) signal) of the subject is detected. At least partially in response thereto, an outcome of treating the subject for a neuropsychiatric condition, using a given therapy is predicted.

The transcranial magnetic stimulation (TMS) pulses may be applied according to any protocol known in the art, including, without limitation, one or more of the protocols known as repetitive TMS, Long Interval Cortical Inhibition (LICI), Short Interval Cortical Inhibition (SICI), contralateral Cortical Silent Period (CSP), paired pulse TMS, and repetitive paired-pulse TMS. Any commercially available TMS device known in the art may be utilized.

For some applications of the present invention, the subject's EEG signal is detected. The power of a given frequency band within the detected EEG signal is calculated. For example, a low gamma frequency band (e.g., a band from approximately 30 Hz (e.g., 30 Hz plus/minus 5 Hz) to approximately 40 Hz (e.g., 40 Hz plus/minus 5 Hz)) may be calculated. For some applications, the low gamma frequency band is normalized by being divided by the power of a different frequency band, such as an alpha frequency band (e.g., a band from approximately 8 Hz (e.g., 8 Hz plus/minus 2 Hz) to approximately 15 Hz (e.g. 15 Hz plus/minus 3 Hz)). At least partially in response to the power of the given frequency band, the outcome of treating the subject for a neuropsychiatric condition, using a given therapy is predicted.

The pulses of TMS can be transmitted to the EEG system (or to a computer processor that receives and processes the EEG signal, e.g., computer processor 16). For some such applications, the EEG signal is analyzed to extract event-related measures, such as event related potentials (ERPs) or event related fields (ERFs). These measures can define evoked responses in the brain, and the evoked responses can be used for identifying activity-related features and for constructing a brain network activity pattern. For some applications, time stamps in the EEG signal are synchronized with the stimulus provided by the TMS pulses to establish a timeline of the response and extract data features responsively to this timeline. Typically, but not necessarily, the collection of the EEG signal is ongoing, such that the signal is collected continuously, before, during and/or after the TMS stimulus.

For some applications, the EEG signal is analyzed immediately after acquisition ("online analysis"), and/or it is recorded and stored, and, thereafter, analyzed ("offline analysis").

Figure 2:
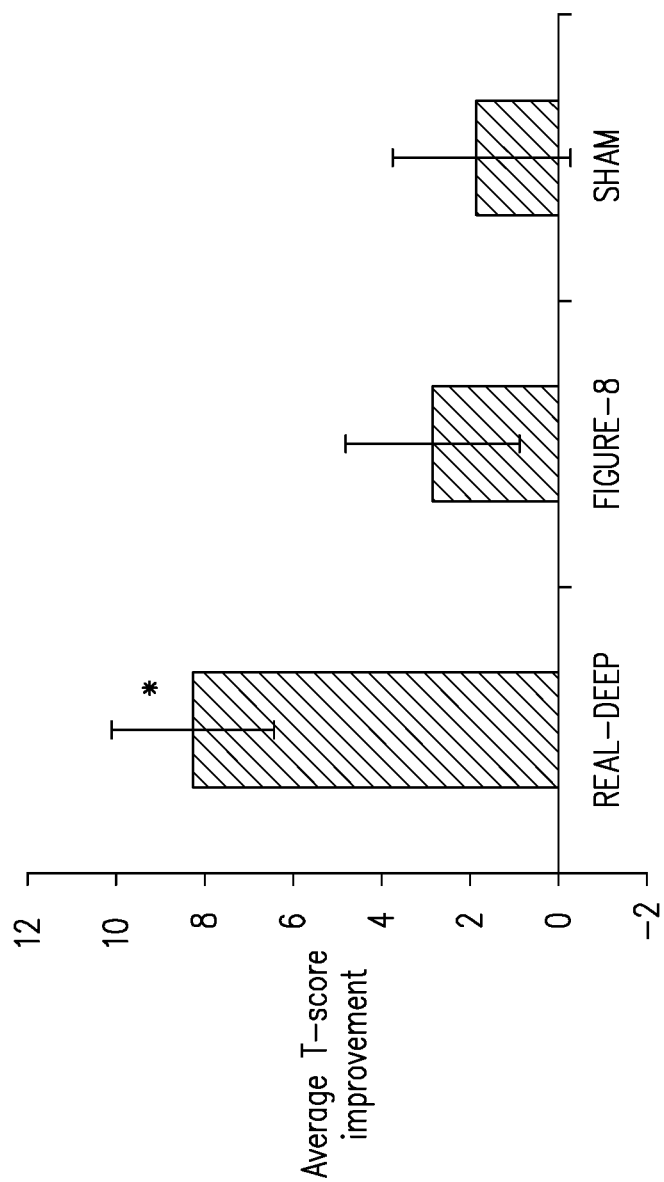
FIG. 2 is a bar chart indicating the responses of ADHD patients to stimulation of the right prefrontal cortex using respective types of transcranial magnetic stimulation coils, which is performed in accordance with some applications of the present invention.

Reference is now made to FIG. 2, which is a bar chart indicating the responses of ADHD patients to stimulation of the right prefrontal cortex using, respectively, (a) a deep transcranial magnetic stimulation (dTMS) coil, (b) a figure-eight transcranial magnetic stimulation (TMS) coil, and (c) a sham TMS coil. The ADHD patients were identified as suffering from ADHD using standard tests, such as Conners' Adult ADHD Rating Scales.

The left-most bar of the bar chart of FIG. 2 shows the results of treating a group of 15 ADHD patients using a dTMS coil. The patients were stimulated using a coil configured to apply dTMS, for example, as described in U.S. Pat. No. 7,407,478 to Zangen, U.S. Pat. No. 8,608,634 to Zangen, and/or US 2014/0235928 to Zangen, all of which references are incorporated herein by reference. 15 daily treatment sessions were applied to each of the patients over a period of three weeks, the treatment being applied over five daily sessions each week. In each of the daily treatments that were applied to each of the patients, 40 stimulation trains were applied to the right prefrontal cortex. Each of the trains had a duration of 2 seconds, and there was a 20 second inter-train interval, between each of the trains. The stimulation was applied at a frequency of 18 Hz.

As shown, on average the dTMS stimulation resulted in an improvement of 8 to the T-score of the patients, the T-scores being measured in accordance with Conners' Adult ADHD Rating Scales. The above results had a p-value of less than 0.05.

The middle bar of the bar chart of FIG. 2 shows the results of treating a group of 11 ADHD patients using a figure-eight stimulation coil. The patients were treated using a generally similar treatment protocol to the above-described protocol. As shown, the stimulation using the figure-eight coil resulted in a lower average improvement to the patients' T-scores than that measured on the patients who were stimulated using a dTMS coil.

The right-most bar of the bar chart of FIG. 2 shows the results of treating a group of 12 ADHD patients using a sham TMS coil. The patients were treated using a generally similar treatment protocol to the above-described protocol. As shown, the stimulation using the sham coil resulted in a lower average improvement to the patients' T-scores than that measured on the patients who were stimulated using a dTMS coil.

The results shown in FIG. 2 indicate that applying dTMS to the pre-frontal cortex may be a suitable treatment for at least some ADHD patients.

In conjunction with the above-described treatments, EEG recordings were taken from the patients, before, during and after the first and the last days of treatment. In addition, EEG recordings were taken (a) during a stop signal task (SST), and (b) following a single TMS pulse applied to the right pre-frontal cortex, using a figure-eight coil.

Figure 3A:
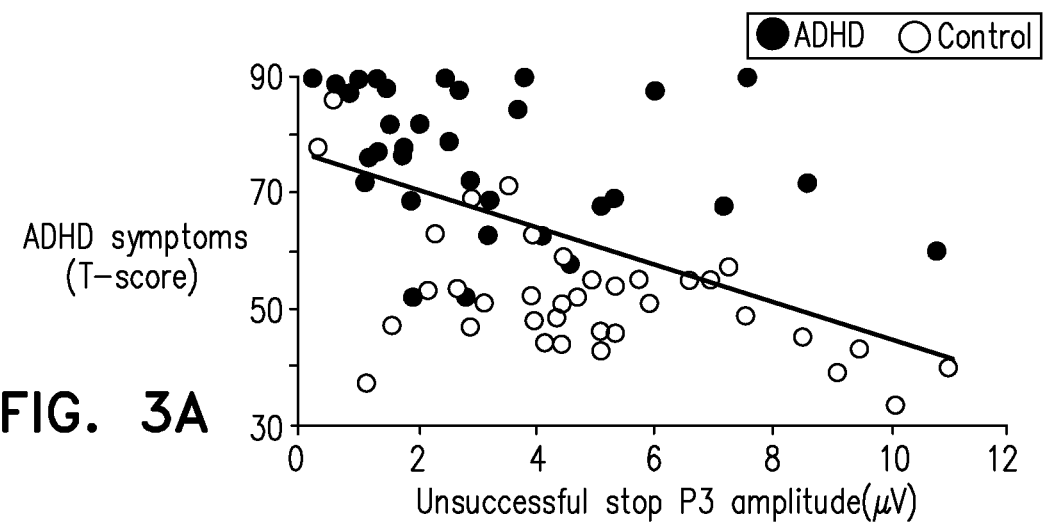
FIGS. 3A, 3B, and 3C are graphs showing the correlation between T-scores of ADHD patients and of healthy subjects to respective indicators, which are calculated in accordance with some applications of the present invention.
Figure 3B:
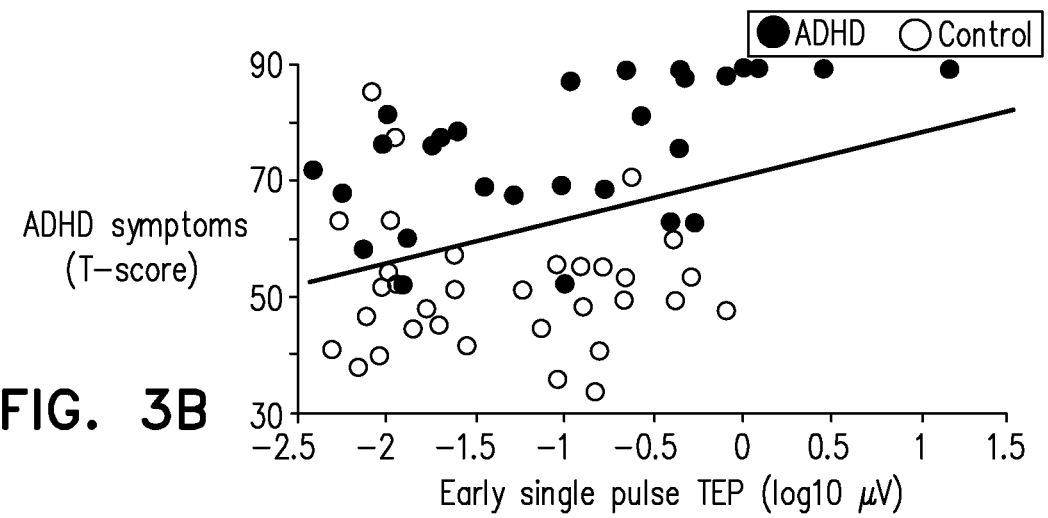
Figure 3C:
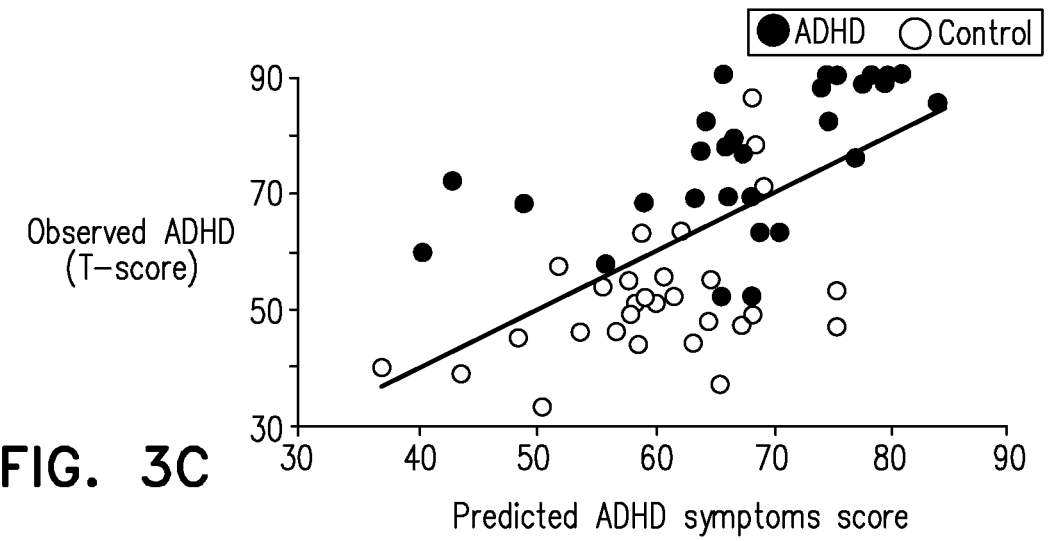

Reference is now made to FIGS. 3A-C, which are graphs showing the correlation between T-scores of ADHD patients and of healthy subjects and respective indicators, in accordance with some applications of the present invention.

At baseline (i.e., before repetitive TMS was applied), event-related potentials of the ADHD patients were recorded during stop signal tasks. As a control, event-related potentials of healthy subjects were also recorded during similar stop signal tasks. It was found that both for successful stops and unsuccessful stops, there was a difference between the amplitudes of components of the event-related potentials of the ADHD patients compared to those of the healthy subjects. For example, substantially lower amplitudes of the N200 and P300 components recorded during the stop signal tasks, were evident in the ADHD patients compared to the healthy subjects.

Reference is now made to FIG. 3A, which is a graph indicating the relationship between the T-scores of both the ADHD patients and the healthy subjects and the P300 amplitude recorded during unsuccessful stop signal tasks performed by the patients/subjects. The P300 amplitude was recorded using frontal central and parietal electrodes. As shown, there is a correlation between the T-scores and the P300 amplitudes, the correlation coefficient being −0.51.

In addition to the above, a single pulse of TMS was applied to the right prefrontal cortex of the ADHD patients and the healthy subjects using a figure-eight coil, following which the patients'/subjects' EEG signals were recorded. It was found that the TMS-evoked potential of the ADHD patients was lower than that of the healthy subjects.

Reference is now made to FIG. 3B, which is a graph indicating the relationship between the T-scores of both the ADHD patients and the healthy subjects and the TMS-evoked potentials ("TEP"). As shown, there is a correlation between the T-scores and the TMS-evoked potentials, the correlation coefficient being −0.39. (It is noted that in FIG. 3B, the correlation between the T-scores of both the ADHD patients and the healthy subjects and the TMS-evoked potentials appears to be positive, but this is because the TMS-evoked potentials were negative, and a logarithmic scale was used to measure the TMS-evoked potentials.)

Reference is now made to FIG. 3C, which is a graph indicating the correlation between the T-scores of both the ADHD patients and the healthy subjects and a predicted ADHD symptoms score, the predicted score being based upon (a) the P300 amplitudes recorded during unsuccessful stop signal tasks performed by the patients/subjects (indicated in FIG. 3A), and (b) the TMS-evoked potentials of the patients/subjects (indicated in FIG. 3B), in a multiple regression model. As shown, there is substantial correlation between the T-scores and the ADHD-indicator, the correlation coefficient being 0.61.

In view of the results shown in FIGS. 3A-C, for some applications of the present invention, TMS is applied to a subject who is suspected of suffering from ADHD. Typically, the TMS is applied at least to the subject's right pre-frontal cortex. The subject's EEG is detected at a given time interval following the TMS stimulation. At least partially in response to a characteristic of the TMS-evoked EEG signal, it is determined whether or not the subject suffers from ADHD, and/or an ADHD score of the subject is calculated. For some applications, in addition to the TMS-evoked potential, event-related potentials are measured during stop signal tasks that are performed by the subject. At least partially in response to (a) a characteristic of the TMS-evoked EEG signal, and (b) a component of the event-related potentials measured during the stop signal tasks, it is determined whether or not the subject suffers from ADHD, and/or an ADHD score of the subject is calculated.

Figure 4:
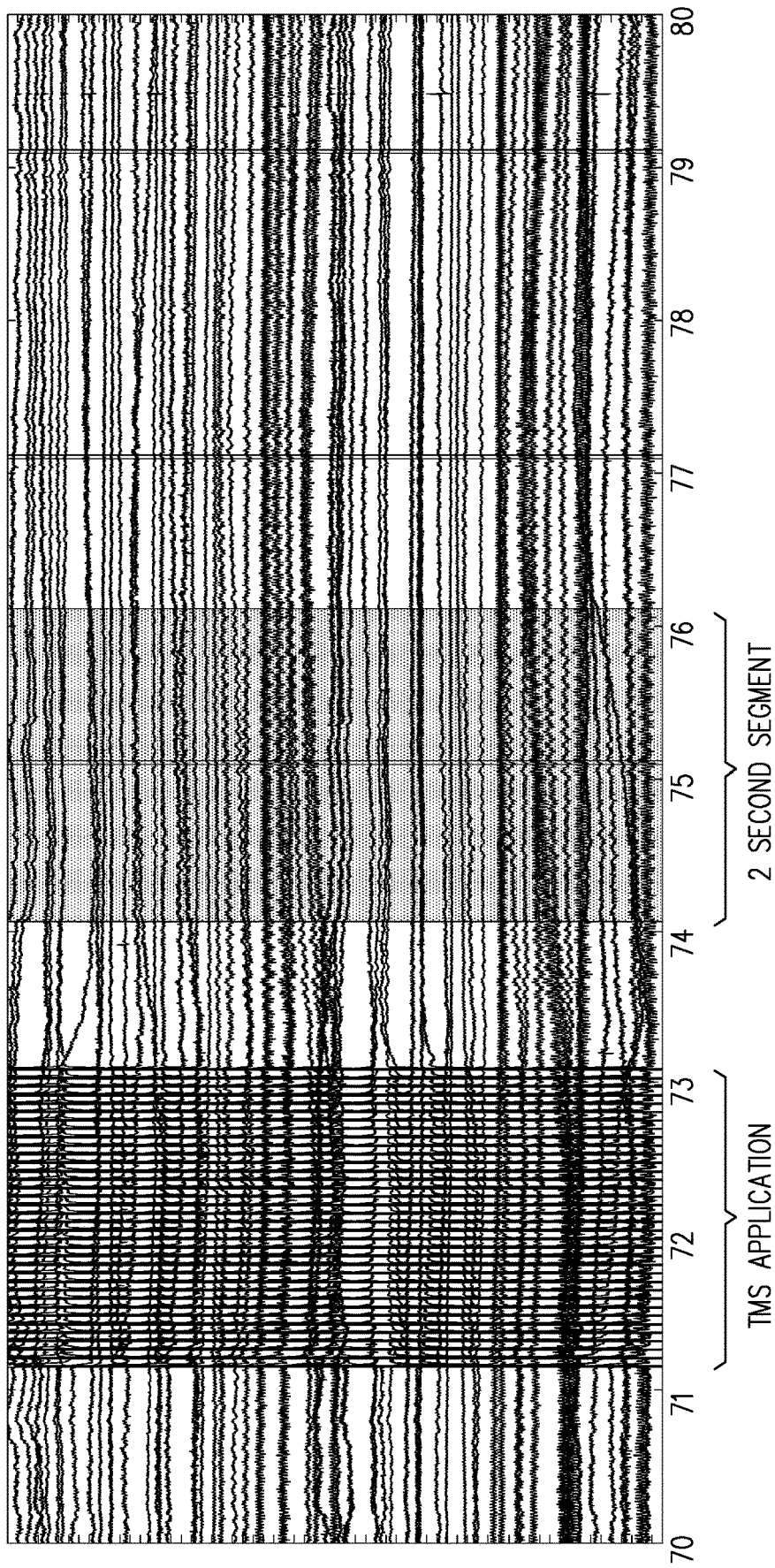
FIG. 4 shows an intra-treatment EEG recording of a subject, from which a two-second-segment is sampled, in accordance with some applications of the present invention.

Reference is now made to FIG. 4, which shows an intra-treatment EEG recording of a subject, in accordance with some applications of the present invention. The recording is from a subject who has ADHD and was recorded while the subject was receiving dTMS in accordance with the stimulation protocol described hereinabove, with reference to FIG. 2. As described hereinabove, in each of the daily treatments, 40 stimulation trains were applied to the subject's right prefrontal cortex. Each of the trains had a duration of 2 seconds, and there was a 20 second inter-train interval, between each of the trains. During the aforementioned treatment, EEG measurements were recorded from the subject.

The EEG recordings from inter-train intervals were sampled over two-second segments. The two-second segments were sampled after at least one second had passed from the end of the previous TMS train, in order to reduce the effects of direct artifacts of the dTMS stimulation on the EEG signal. FIG. 4 shows an example of such a sampling, a two second segment being shown to be sampled approximately one second after the end of the previous TMS train. (Although the two-second interval shown in FIG. 4 is shown as commencing 1 second after the end of the previous dTMS train, the characteristics of the EEG sample that are described hereinbelow, were also exhibited by samples that were sampled within inter-train intervals, but after a greater time had elapsed since the end of the previous dTMS train.)

As described hereinabove with reference to FIG. 2, TMS (using a dTMS coil, a figure-eight coil, or a sham coil) was applied to ADHD patients for 15 days. The patients' intra-treatment EEG signals were recorded on the first, eighth and fifteenth days of the days on which the TMS was applied. Two-second interval sections of the inter-treatment EEG signals were sampled, as shown in FIG. 4, and the samples were spectrally analyzed, such that the powers of respective frequency components within the samples were calculated. At the end of the treatments, the patients' T-scores were measured in order to measure the responsiveness of the patients to the TMS treatments. The responsiveness of the patients to the treatment was then compared to the power of the respective frequency components of the two-second interval EEG samples as recorded at the first treatment session (i.e., as recorded during the TMS that was applied on the first day of the treatment).

Figure 5:
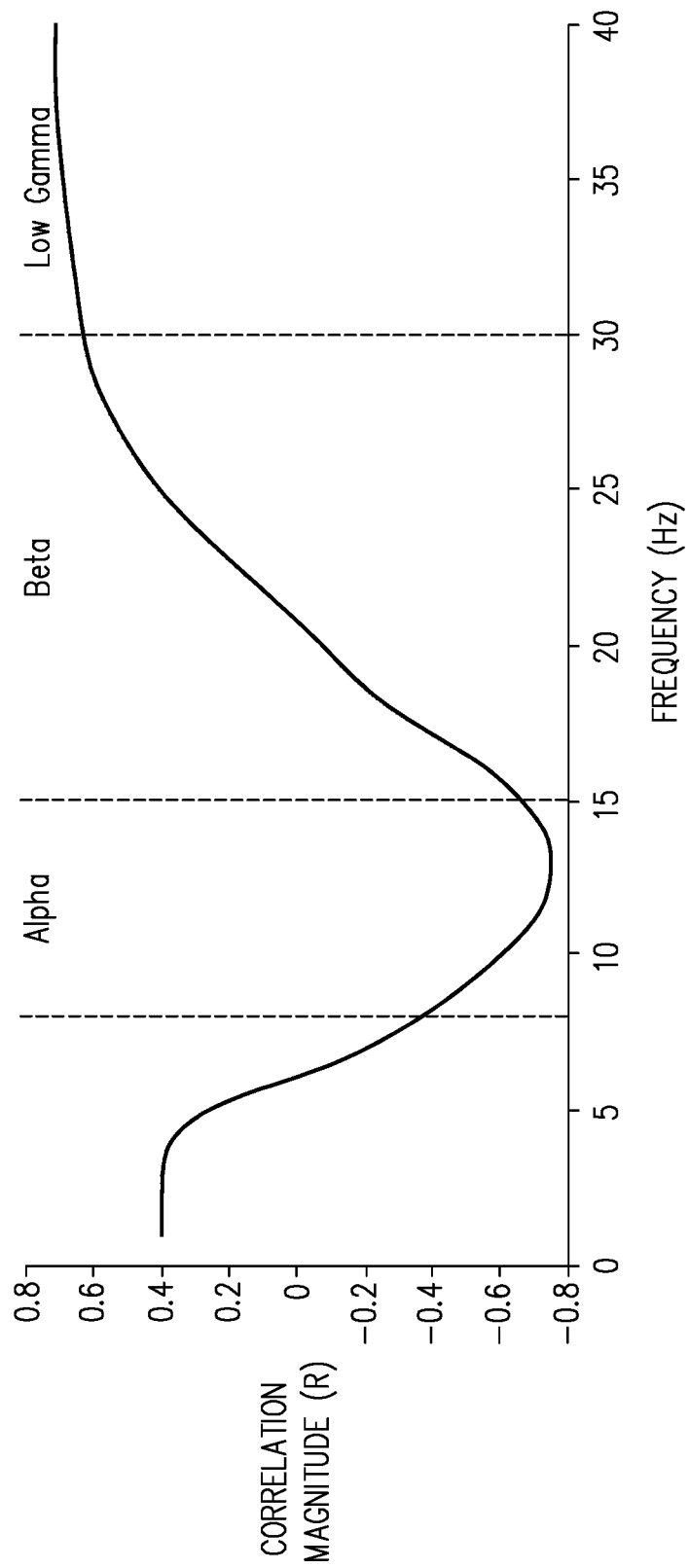
FIG. 5 is a graph indicating, for ADHD patients to whom deep transcranial magnetic stimulation was applied, the degree of correlation between (a) improvements to patients' T-scores, and (b) the power of respective frequency components of two-second interval EEG samples as recorded at an initial treatment session, in accordance with some applications of the present invention.

Reference is now made to FIG. 5, which is a graph indicating, for the ADHD patients to whom dTMS was applied, the degree of correlation between (a) improvements to patients' T-scores, and (b) the power of respective frequency components of the two-second interval EEG samples as recorded at the FC4 EEG electrode at the first treatment session. As shown, there is a correlation between many frequency components of the two-second interval EEG samples as recorded at the first treatment session and the improvements to the patients' T-scores. It is noted that although the EEG signals from which the samples were taken and spectrally analyzed were recorded at the first treatment session of a three-week course of treatment, the graph shown in FIG. 5 indicates that there is a correlation between the power of certain frequency components of the sample and the responsiveness of the patients to the treatment, as measured after the three-week course of treatment.

The graph shown in FIG. 5 indicates that an electrophysiological signal of a subject recorded within a given time period after applying TMS to the subject may serve as an indicator of the responsiveness of the subject to treating the subject for a given neuropsychiatric condition using a given therapy. Therefore, for some applications of the present invention computer processor 16 (FIG. 1) drives transcranial magnetic stimulation device 10 to apply one or more pulses (e.g., one or more trains) of transcranial magnetic stimulation to a subject. Within a given time period of applying one of the pulses of transcranial magnetic stimulation to the subject, the computer processor detects an electrophysiological signal of the subject, using the electrophysiological signal detecting electrodes 14. At least partially in response thereto, the computer processor predicts an outcome of treating the subject for a neuropsychiatric condition, using a given therapy. For some applications, the computer processor generates an output on an output device (such as monitor 18) in response to the predicted outcome. For example, the EEG signal of a patient suffering from ADHD may be recorded a given time period after applying a TMS or dTMS train to the subject, or during the application of a TMS or dTMS train to the subject. In response thereto, the responsiveness of the patient to using TMS or dTMS to treat the patient for ADHD is predicted.

In EEG spectral analysis, the frequency range of approximately 8 Hz (e.g., 8 Hz plus/minus 2 Hz) to approximately 15 Hz (e.g., 15 Hz plus/minus 3 Hz) is described as the alpha band, the range of approximately 15 Hz (e.g., 15 Hz plus/minus 3 Hz) to approximately 30 Hz (e.g., 30 Hz plus/minus 5 Hz) is described as the beta band, and the frequency range of approximately 30 Hz (e.g., 30 Hz plus/minus 5 Hz) to approximately 100 Hz (e.g., 100 Hz plus/minus 10 Hz) is described as the gamma band. These categorizations are indicated upon the graph shown in FIG. 5. Within the context of the present application, the frequency range of approximately 30 Hz (e.g., 30 Hz plus/minus 5 Hz) to approximately 40 Hz (e.g., 40 Hz plus/minus 5 Hz) is further categorized as the low-gamma band.

Figure 6A:
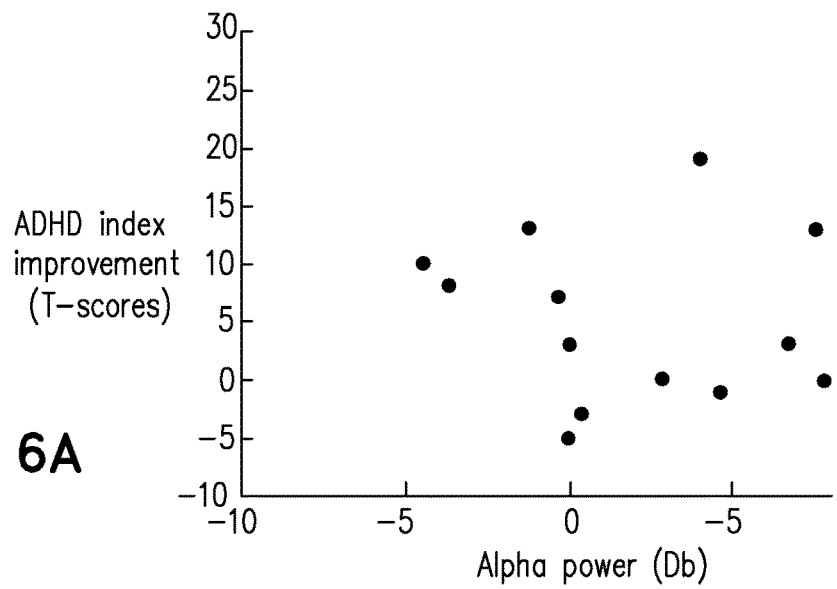
FIGS. 6A, 6B, and 6C are graphs showing the relationship between improvements to T-scores of ADHD patients, and the power of the alpha frequency band of an intra-treatment EEG that was recorded on the first day of a treatment, for patients that were treated using, respectively, a sham coil (FIG. 6A), a figure-eight coil (FIG. 6B), and a dTMS coil (FIG. 6C)
Figure 6B:
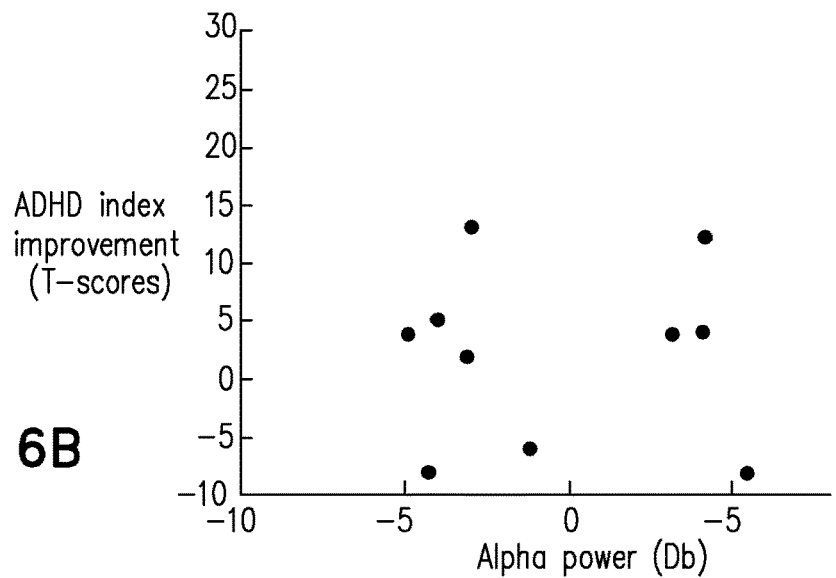
Figure 6C:
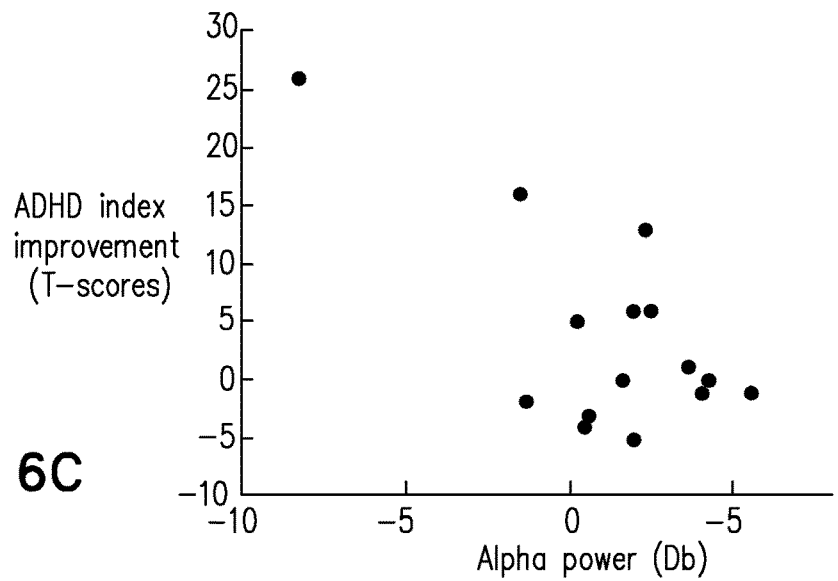

Reference is now made to FIGS. 6A-C, which are graphs showing the relationship between improvements to T-scores of ADHD patients, and the power of the alpha frequency band of an intra-treatment EEG that was recorded at the FC4 EEG electrode on the first day of a treatment, sampled as described hereinabove, for patients that were treated using, respectively, a sham coil (FIG. 6A), a figure-eight coil (FIG. 6B), and a dTMS coil (FIG. 6C).

Reference is also made to FIGS. 7A-C, which are graphs showing the relationship between improvements to T-scores of ADHD patients, and the power of the beta frequency band of an intra-treatment EEG that was recorded at the FC4 EEG electrode on the first day of a treatment, sampled as described hereinabove, for patients that were treated using, respectively, a sham coil (FIG. 7A), a figure-eight coil (FIG. 7B), and a dTMS coil (FIG. 7C).

Figure 8A:
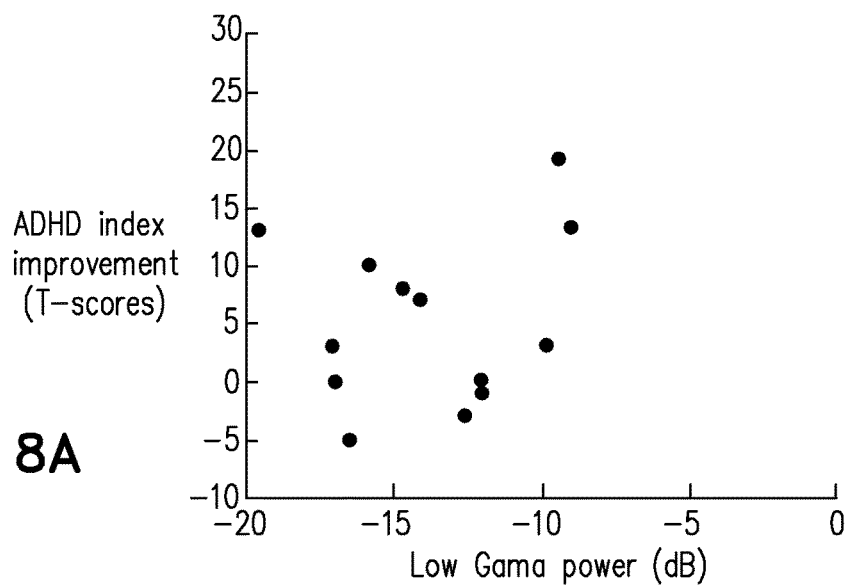
FIGS. 8A, 8B, and 8C are graphs showing the relationship between improvements to T-scores of ADHD patients, and the power of the low gamma frequency band of an intra-treatment EEG that was recorded on the first day of a treatment, for patients that were treated using, respectively, a sham coil (FIG. 8A), a figure-eight coil (FIG. 8B), and a dTMS coil (FIG. 8C)
Figure 8B:
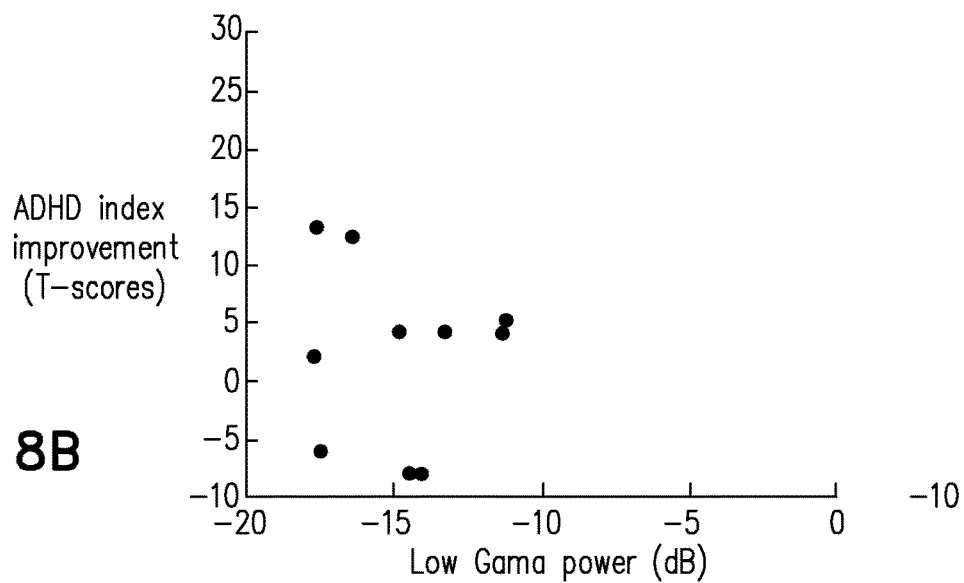
Figure 8C:
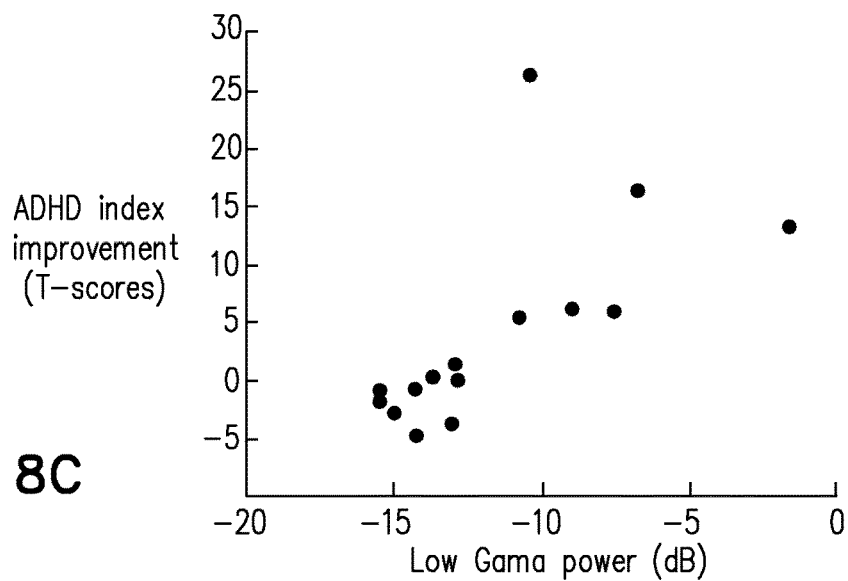

Reference is additionally made to FIGS. 8A-C, which are graphs showing the relationship between improvements to T-scores of ADHD patients, and the power of the low gamma frequency band of an intra-treatment EEG that was recorded at the FC4 EEG electrode on the first day of a treatment, sampled as described hereinabove, for patients that were treated using, respectively, a sham coil (FIG. 8A), a figure-eight coil (FIG. 8B), and a dTMS coil (FIG. 8C).

Figure 9A:
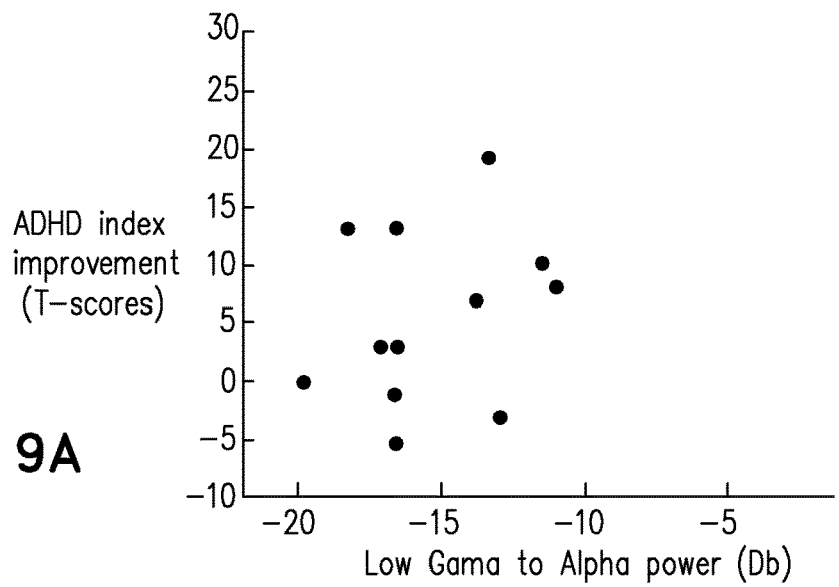
FIGS. 9A, 9B, and 9C are graphs showing the relationship between improvements to T-scores of ADHD patients, and a ratio of the power of the low gamma frequency band of an intra-treatment EEG that was recorded on the first day of a treatment to the power of the alpha frequency band of the EEG recording, for patients that were treated using, respectively, a sham coil (FIG. 9A), a figure-eight coil (FIG. 9B), and a dTMS coil (FIG. 9C)
Figure 9B:
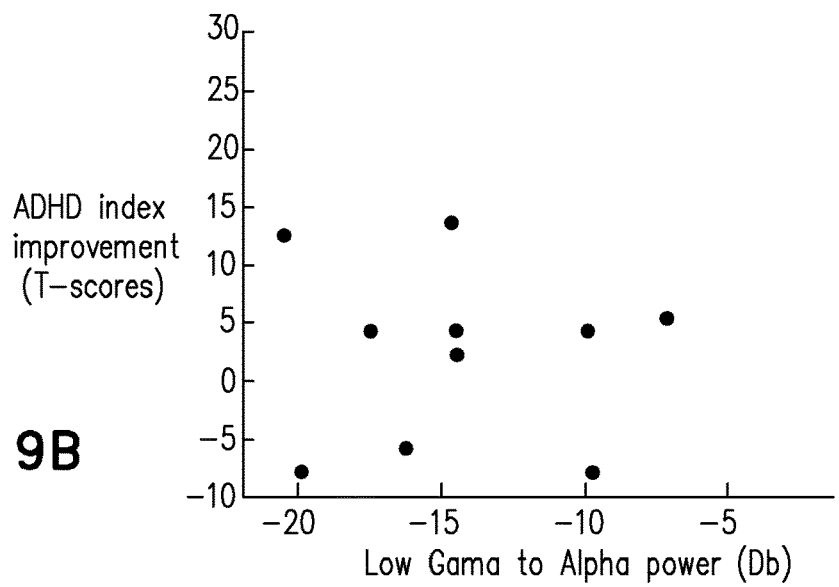
Figure 9C:
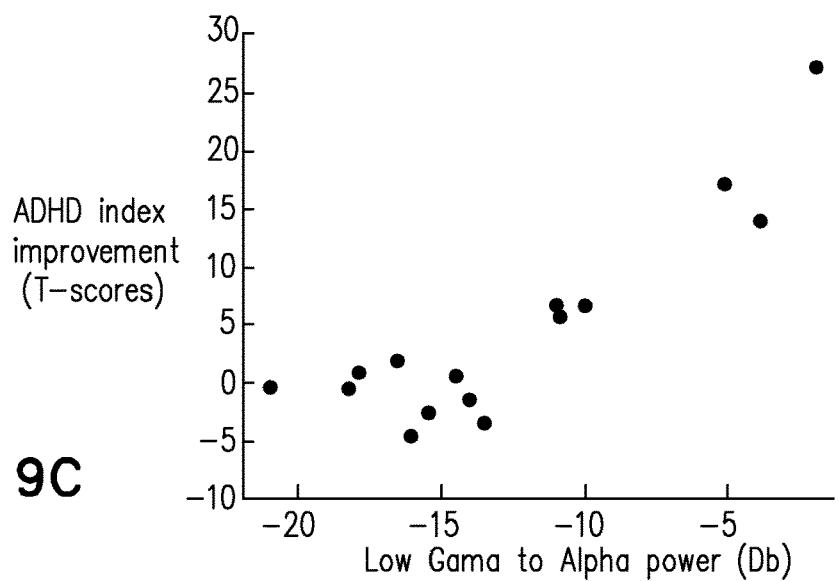

Reference is further made to FIGS. 9A-C, which are graphs showing the relationship between (a) improvements to T-scores of ADHD patients, and (b) the power of the low gamma frequency band of an intra-treatment EEG that was recorded at the FC4 EEG electrode on the first day of a treatment, sampled as described hereinabove, and normalized by the power of the alpha frequency band using a decibel scale, for patients that were treated using, respectively, a sham coil (FIG. 9A), a figure-eight coil (FIG. 9B), and a dTMS coil (FIG. 9C).

It may be observed that, when the patients are treated using a dTMS coil (corresponding to the graphs shown in FIGS. 6C, 7C, and 8C), then at each of the frequency bands, there is a degree of correlation between the power of the frequency band on the first day of treatment and the improvement to the patients' T-scores resulting from the treatment. By contrast, when the patients are treated using a sham TMS coil or a figure-eight TMS coil (corresponding to the graphs shown in FIGS. 7A-B, 7A-B, and 8A-B), then at each of the frequency bands, there is no substantial correlation between the power of the frequency band on the first day of treatment and the improvement to the patients' T-scores resulting from the treatment.

Furthermore, by comparing FIG. 9C to FIGS. 6C, 7C, and 8C, it may be observed that when stimulated using a dTMS coil, the correlation to the improvements to the T-scores exhibited by (a) the power of the low gamma band normalized by the power of the low alpha band is relatively strong compared to that of (b) the alpha band (FIG. 6C), the beta band (FIG. 7C) and the low gamma band (FIG. 8C).

It was observed during the above-described experiments that, in general, stimulation using a dTMS coil caused EEG recordings subsequent to the stimulation to have a high ratio of low gamma power to alpha power (e.g., up to 4 dB) in the prefrontal cortex region, when normalized by subtracting the effects of a sham coil. Stimulation using a figure-eight coil also caused there to be a high ratio of low gamma power to alpha power in certain regions of the brain, but the effect was less than that exhibited by patients stimulated with dTMS coils.

Based upon the above described experimental results, for some applications of the present invention, computer processor 16 detects an EEG signal of the subject, using EEG electrodes. The computer processor calculates the power of a given frequency band within the detected EEG signal. At least partially in response to the power of the given frequency band, the computer processor predicts an outcome of treating the subject for a neuropsychiatric condition, using a given therapy. For some applications, the computer processor generates an output on an output device (such as monitor 18) in response to the predicted outcome. For example, the EEG signal of a patient suffering from ADHD may be recorded (e.g., after applying dTMS to the subject). The power of a given frequency band (e.g., the alpha band, or the low gamma band) is calculated, and in response thereto, the responsiveness of the patient to using dTMS to treat the patient for ADHD is predicted. For some applications, the powers of two or more frequency bands are combined and/or manipulated using a mathematical operation. For some applications, the power of the given frequency band is normalized by dividing the power of the given frequency band by that of a different frequency band. For example, the low gamma frequency band may be normalized by being divided by the power of a different frequency band, such as an alpha frequency band. Alternatively or additionally, the powers of two or more frequency bands may be combined and/or manipulated using a different mathematical operation.

It is noted that the results described with reference to FIGS. 6A-C, 7A-C, 8A-C, and 9A-C indicate that the responsiveness of an ADHD patient to treatment using dTMS may be predicted based upon recordings from the FC4 electrode of an EEG recording on the first day of treatment. However, during the course of the above-described experiments it was observed that at locations of EEG electrodes other than the FC4 electrode location there also appeared to be correlations between the responsiveness of patients to treatment and the power of frequency bands of the EEG signal on the first day of treatment. In addition, this effect was observed during treatment with a figure-eight coil and not just using a dTMS coil. Therefore, the scope of the present invention includes using the apparatus and techniques described herein using any type of transcranial magnetic stimulation parameters, and any type of electrophysiological sensing, including EEG sensing, at any position, mutatis mutandis.

For some application of the present invention, computer processor 16 detects an electrophysiological signal (typically, an electroencephalography (EEG) signal) of the subject, using electrodes 14. For some applications, activity-related features are identified in the EEG signal, and a brain network activity (BNA) pattern is constructed based on those features. At least partially in response to the brain network activity, the computer processor predicts an outcome of treating the subject for a neuropsychiatric condition, using a given therapy. For some applications, the computer processor generates an output on an output device (such as a display) in response to the predicted outcome.

Figure 10A:
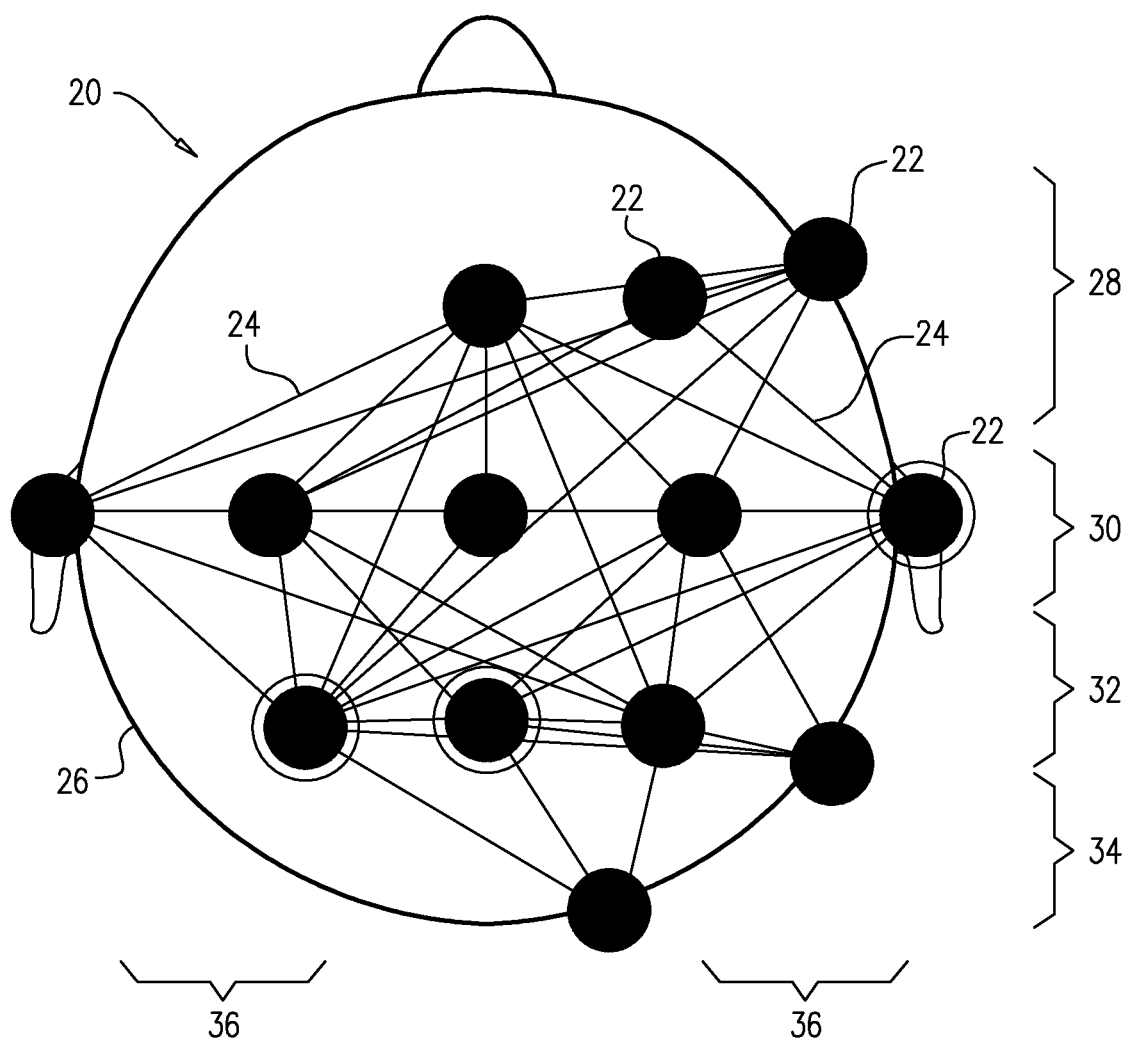
FIG. 10A is a schematic illustration showing a representative example of a brain network activity (BNA) pattern which can be extracted from EEG data, in accordance with some applications of the present invention.

The concept of brain network activity pattern can be better understood with reference to FIG. 10A which is a representative example of a brain network activity pattern 20 which may be extracted from the TMS-evoked EEG signal, according to some applications of the present invention. Brain network activity pattern 20 has a plurality of nodes 22, each representing an activity-related feature. For example, a node can represent a particular frequency band (optionally two or more particular frequency bands) at a particular location and within a particular time-window or latency range, optionally with a particular range of amplitudes.

Some of nodes 22 are connected by edges 24 each representing the causal relationship between the nodes at the ends of the respective edge. Thus, the brain network activity pattern is a represented as a graph having nodes and edges. In some applications of the invention the brain network activity pattern includes a plurality of discrete nodes, wherein information pertaining to features of the data is represented only by the nodes and information pertaining to relationships between the features is represented only by the edges.

FIG. 10A illustrates brain network activity pattern 20 within a template 26 of a scalp, demonstrating the relationship between the locations of the nodes and lobes of the brain (frontal 28, central 30, parietal 32, occipital 34 and temporal 36). The nodes in the brain network activity pattern can be labeled by their various characteristics. A color coding or shape coding visualization technique can also be employed, if desired. For example, nodes corresponding to a particular frequency band can be displayed using one color or shape and nodes corresponding to another frequency band can be displayed using another color or shape. For example, red nodes may be used to correspond to Delta waves and green nodes to correspond to Theta waves. As shown in FIG. 10A, "red" nodes are illustrated with solid black circles, and "green" nodes are illustrated with a solid black circle surrounded by an outer circle (of which there are three in FIG. 10A).

Brain network activity pattern 20 can describe brain activity of a single subject or a group or sub-group of subjects. A brain network activity pattern that describes the brain activity of a single subject is referred to herein as a subject-specific brain network activity pattern, and a brain network activity pattern that describes the brain activity of a group or sub-group of subjects is referred to herein as a group brain network activity pattern.

When brain network activity pattern 20 is a subject-specific brain network activity pattern, only vectors extracted from data of a given subject are used to construct the brain network activity pattern for that subject. Thus, each node corresponds to a point in the multidimensional space and therefore represents an activity event in the brain. When brain network activity pattern 20 is a group brain network activity pattern, some nodes can correspond to a cluster of points in the multidimensional space, and the pattern therefore represents an activity event which is prevalent in the group or sub-group of subjects. Due to the statistical nature of a group brain network activity pattern, the number of nodes (referred to herein as the "order") and/or edges (referred to herein as the "size") in a group brain network activity pattern is typically, but not necessarily, larger than the order and/or size of a subject-specific brain network activity pattern.

Figure 10B:
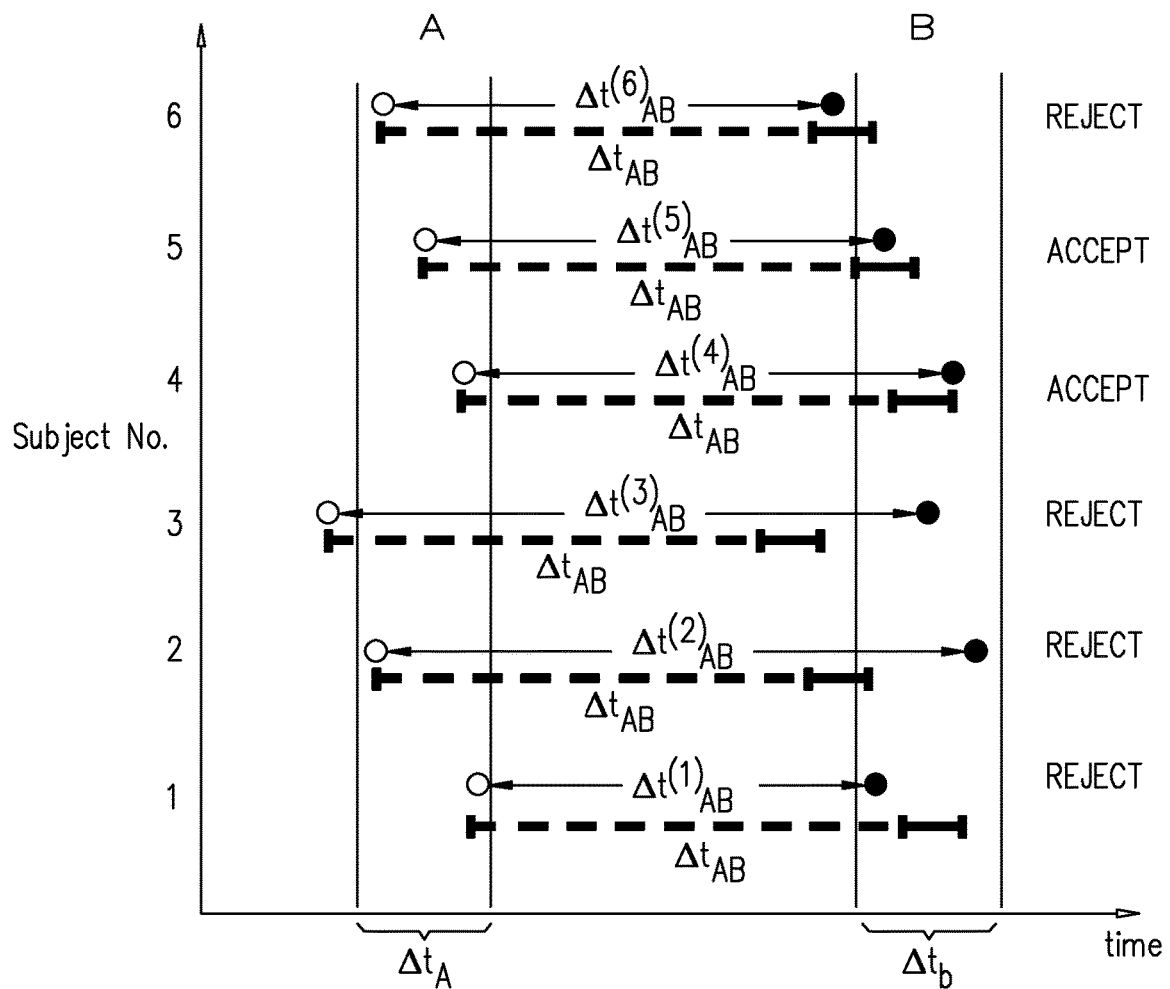
FIG. 10B shows a representation of times at which respective unitary events within the EEG signals of respective subjects took place, in accordance with some applications of the present invention.

As an example for constructing a group brain network activity pattern, the simplified scenario illustrated in FIG. 10B is considered, wherein a "segment" corresponds to a different subject in a group or sub-group of subjects. The EEG signals of the group include, in the present example, two unitary events associated with locations A and B. Each of these events forms a cluster in the multidimensional space. In some applications of the invention, each of the clusters, referred to herein as clusters A and B, is represented by a node in the group brain network activity pattern. The two clusters A and B are identified as activity-related features since there are some individual points within these clusters that pass the criteria for such a relationship (the pairs of Subject Nos. 4 and 5, in the present example, as will be explained in further detail below). Thus, for some applications of the invention, the nodes corresponding to clusters A and B are connected by an edge. A simplified illustration of the resulting group brain network activity pattern is illustrated in FIG. 10C.

A subject-specific brain network activity pattern is typically constructed by comparing the features and relations among features of the EEG signal collected from the subject to the features and relations among features of reference data, which, for some applications, correspond to EEG signals of the group. For such applications, points and relationships among points associated with the subject's signal are compared to clusters and relationships among clusters associated with the group's data. Consider, for example, the simplified scenario illustrated in FIG. 10B, wherein a "segment" corresponds to a different subject in a group or sub-group of subjects. Cluster A does not include a contribution from Subject No. 3, and cluster B does not include a contribution from Subject No. 6, since for these subjects the respective points fail to pass the time-window criterion. Thus, for some applications, when a subject-specific brain network activity pattern is constructed for Subject No. 3 it does not include a node corresponding to location A, and when a subject-specific brain network activity pattern is constructed for Subject No. 6 it does not include a node corresponding to location B.

On the other hand, both locations A and B are represented as nodes in the subject-specific brain network activity patterns constructed for any of Subject Nos. 1, 2, 4 and 5. For those subjects for which the respective points are accepted as a pair of activity-related features (e.g., due to the events taking place within a given time interval from one another, corresponding to Subject Nos. 4 and 5, in the present example), the corresponding nodes are connected by an edge. A simplified illustration of a subject-specific brain network activity pattern for such a case is shown in FIG. 10D.

Figure 10C:
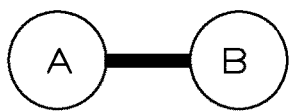
FIGS. 10C, 10D, and 10E shows respective examples of pairs of nodes and corresponding edges of a brain network activity pattern, in accordance with some applications of the present invention.
Figure 10D:
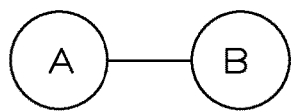

Note that for this simplified example of only two nodes, the subject-specific brain network activity pattern of FIG. 10D is similar to the group brain network activity pattern of FIG. 10C. For a larger number of nodes, the order and/or size of the group brain network activity pattern is, as stated, typically larger than the order and/or size of the subject-specific brain network activity pattern. An additional difference between the subject-specific and group brain network activity patterns can be manifested by the degree of relation between the activity-related features represented by the edges, as further detailed hereinbelow.

Figure 10E:
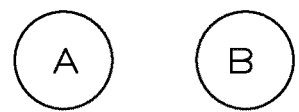

For subjects for which the points were rejected from being viewed as a pair of activity-related features (Subject Nos. 1 and 2, in the present example), the corresponding nodes are not connected by an edge. A simplified illustration of a subject-specific brain network activity pattern for such cases is shown in FIG. 10E.

It is to be understood, however, that although the above technique for constructing a subject-specific brain network activity pattern is described in terms of the relationship between the signal of a particular subject to the data of a group of subjects, this need not necessarily be the case, since for some applications, a subject-specific brain network activity pattern can be constructed only from the EEG signals obtained from a single subject. For such applications, vectors of waveform characteristics are extracted separately for time-separated TMS stimuli, to define clusters of points where each point within the cluster corresponds to a response to a stimulus applied at a different time, as further detailed hereinabove. The procedure for constructing subject-specific brain network activity patterns in such applications is typically generally similar to the procedure for constructing a group brain network activity pattern described above. However, since all signals are collected from a single subject, the brain network activity pattern is subject-specific.

Thus, in accordance with some applications, a subject-specific brain network activity pattern is generated that is of one of two types: a first type that describes the association of the particular subject to a group or sub-group of subjects, which is a manifestation of a group brain network activity pattern for the specific subject, and a second type that describes the data of the particular subject without associating the subject to a group or sub-group of subjects. The former type of brain network activity pattern is referred to herein as an associated subject-specific brain network activity pattern, and the latter type of brain network activity pattern is referred to herein as an unassociated subject-specific brain network activity pattern.

For unassociated subject-specific brain network activity patterns, the analysis is typically performed on a set of evoked responses. Typically, the data is then averaged and a single vector of the data is generated. For group brain network activity patterns, on the other hand, the data of each subject of the group is typically averaged and thereafter turned into vectors of the data.

It is noted that, while an unassociated subject-specific brain network activity pattern is typically unique for a particular subject (at the time the subject-specific brain network activity pattern is constructed), the same subject may be characterized by more than one associated subject-specific brain network activity patterns, since a subject may have different associations to different groups. Consider for example a group of healthy subjects and a group of non-healthy subjects all suffering from the same brain disorder. Consider further a subject Y, who may or may not belong to one of those groups. One or more of several subject-specific brain network activity patterns for subject Y may be generated, in accordance with respective applications of the present invention.

A first brain network activity pattern is an unassociated subject-specific brain network activity pattern, which, as stated, is generally unique for this subject, since it is constructed from data collected only from subject Y. A second brain network activity pattern is an associated subject-specific brain network activity pattern constructed in terms of the relationship between the data of subject Y to the data of the healthy group. A third brain network activity pattern is an associated subject-specific brain network activity pattern constructed in terms of the relation between the data of subject Y to the data of the non-healthy group. Each of these brain network activity patterns is useful for assessing the condition of subject Y. The first brain network activity pattern can be useful, for example, for monitoring changes in the brain function of the subject over time (e.g., monitoring brain plasticity or the like) since it allows comparing the brain network activity pattern to a previously constructed unassociated subject-specific brain network activity pattern. The second and third brain network activity patterns can be useful for determining the level of association between subject Y and the respective groups, thereby determining the likelihood of brain disorder for the subject.

For some additional applications, the reference data used for constructing the subject-specific brain network activity pattern correspond to historic data previously acquired from the same subject. Such applications are performed in a generally similar manner to the applications described above regarding the generation of an associated subject-specific brain network activity pattern, except that the brain network activity pattern is associated with the history of the same subject instead of being associated with a group of subjects.

For some applications, reference data corresponding to data acquired from the same subject at some later time are used. Such applications allow investigating whether data acquired at an early time evolve into the data acquired at the later time. A particular and non-limiting example is the case of several treatment sessions, e.g., N sessions, for the same subject. Data acquired in the first several treatment sessions (e.g., from session 1 to session k1<N) can be used as reference data for constructing a first associated subject-specific brain network activity pattern corresponding to mid sessions (e.g., from session k2>k1 to session k3>k2), and data acquired in the last several treatment sessions (e.g., from session k4 to session N) can be used as reference data for constructing a second associated subject-specific brain network activity pattern corresponding to the aforementioned mid sessions, where 1<k1<k2<k3<k4. Two such associated subject-specific brain network activity patterns for the same subject can be used for determining data evolution from the early stages of the treatment to the late stages of the treatment.

For some applications, TMS pulses are applied to each of a group of subjects over a multi-session treatment period. For some such applications, a reference group brain network activity pattern is constructed from EEG signals obtained from the subjects of the group on the first session (e.g., the first day, when each session occurs on a different day), and typically based on a single pulse TEP. The inventors of the present applications have found that a single pulse TEP during the first session has a marginal effect on the brain, so that an EEG signal obtained after such pulse can be considered as corresponding to an untreated subject. The reference group brain network activity pattern can be used as a basis for constructing, for one or more of the subjects in the group, an associated subject-specific brain network activity pattern describing the association or lack of association of the particular subject to the group. Such an associated subject-specific brain network activity pattern can be constructed for the particular subject also in one or more subsequent sessions, thereby showing the effect of the treatment relative to the effect of the single pulse TEP during the first session.

Typically, a connectivity weight is assigned to each pair of nodes in the brain network activity pattern (or, equivalently, to each edge in the brain network activity) pattern, thereby providing a weighted brain network activity pattern. The connectivity weight is represented in FIGS. 10A, 10C and 10D by the thickness of the edges connecting two nodes. For example, thicker edges can correspond to higher weights and thinner edges can correspond to lower weights.

For some applications, the connectivity weight includes a weight index calculated based on at least one of the following cluster properties: (i) the number of subjects participating in the corresponding cluster pair, wherein greater weights are assigned for larger number of subjects; (ii) the difference between the number of subjects in each cluster of the pair (referred to as the "differentiation level" of the pair), wherein greater weights are assigned for lower differentiation levels; (iii) the width of the time windows associated with each of the corresponding clusters (see, e.g., $\Delta t_A$ and $\Delta t_B$ in FIG. 10B), wherein greater weights are assigned for narrower windows; (iv) the latency difference between the two clusters (see, e.g., $\Delta t_{AB}$ in FIG. 10A), wherein greater weights are assigned for narrower windows; (v) the amplitude of the signal associated with the corresponding clusters; (vi) the frequency of the signal associated with the corresponding clusters; and (vii) the width of a spatial window defining the cluster (for applications in which the coordinate system is continuous). For any of the cluster properties, except properties (i) and (ii), one or more statistical observables of the property, such as, but not limited to, average, median, supremum, infimum and variance over the cluster are typically used.

For a group brain network activity pattern or an unassociated subject-specific brain network activity pattern, the connectivity weight typically equals the weight index as calculated based on the cluster properties.

For an associated subject-specific brain network activity pattern, the connectivity weight of a pair of nodes is preferably assigned based on the weight index (denoted WI), as well as one or more subject-specific and pair-specific quantities (denoted SI). Representative examples of such quantities are provided below.

In some embodiments of the invention, a pair of nodes of the associated subject-specific brain network activity pattern is assigned with a connectivity weight which is calculated by combining WI with SI. For example, the connectivity weight of a pair in the associated subject-specific brain network activity pattern can be given by WI·SI. For some applications, when a plurality of quantities (e.g., N quantities) are calculated for a given pair of nodes, the pair can be assigned with more than one connectivity weights, e.g., $WI \cdot SI_1$, $WI \cdot SI_2$, ..., $WI \cdot SI_N$, wherein $SI_1$, $SI_2$, ..., $SI_N$, are N calculated quantities. Alternatively or additionally, all connectivity weights of a given pair are combined, e.g., by averaging, multiplying and the like.

The quantity SI can be, for example, a statistical score characterizing the relationship between the subject-specific pair and the corresponding clusters. The statistical score can be of any type, including, without limitation, deviation from average, absolute deviation, standard-score and the like. The relationship for which the statistical score is calculated can pertain to one or more properties used for calculating the weight index, including, without limitation, latency, latency difference, amplitude, frequency and the like.

A statistical score pertaining to latency or latency difference is referred to herein as a synchronization score and denoted SIs. Thus, a synchronization score according to some applications of the present invention is obtained by calculating a statistical score for (i) the latency of the point as obtained for the subject (e.g., $t^{(i)}_A$ and $t^{(i)}_B$, in the above example) relative to the group-average latency of the corresponding cluster, and/or (ii) the latency difference between two points as obtained for the subject (e.g., $\Delta t^{(i)}_{AB}$), relative to the group-average latency difference between the two corresponding clusters.

A statistical score pertaining to amplitude is referred to herein as an amplitude score and denoted SIa. Thus, an amplitude score according to some applications of the present invention is obtained by calculating a statistical score for the amplitude, as obtained for the subject, relative to the group-average amplitude of the corresponding cluster.

A statistical score pertaining to frequency is referred to herein as a frequency score and denoted SIf. Thus, a frequency score according to some applications of the present invention is obtained by calculating a statistical score for the frequency, as obtained for the subject, relative to the group-average frequency of the corresponding cluster.

A statistical score pertaining to the location is referred to herein as a location score and denoted SIl. Using such a score is typically useful for applications in which a continuous coordinate system is employed, as further detailed hereinabove. Thus, a location score according to some applications of the present invention is obtained by calculating a statistical score for the location, as obtained for the subject, relative to the group-average location of the corresponding cluster.

Calculation of statistical scores pertaining to other properties is not excluded from the scope of the present invention.

The following is a description of a technique for calculating the quantity SI, according to some applications of the present invention.

When SI is a synchronization score (SIs) the calculation is typically based on the discrete time points matching the spatiotemporal constraints set by the electrode pair (Time$_{subj}$), if such exist. In these applications, the times of these points are compared to the mean and standard deviation of the times of the discrete points participating in the group pattern (Time$_{pat}$), for each region to provide a regional synchronization score SIs$_r$. The synchronization score SIs can then be calculated, for example, by averaging the regional synchronization scores of the two regions in the pair. Formally, this procedure can be written as:

$$SIs_r = 0.5 + \frac{std(Time_{pat})}{2*(abs(Time_{pat} - Time_{subj}) + std(Time_{pat}))}; SIs = \frac{1}{r}\sum SIs_r$$

An amplitude score SIa, is typically calculated in a similar manner. Initially, the amplitude of the discrete points of the individual subject (Amp$_{subj}$) is compared to the mean and standard deviation of the amplitudes of the discrete points participating in the group pattern (Amp$_{pat}$), for each region to provide a regional amplitude score SIa$_r$. The amplitude score can then be calculated, for example, by averaging the regional amplitude scores of the two regions in the pair:

$$SIa_r = 0.5 + \frac{std(Amp_{pat})}{2*(abs(Amp_{pat} - Amp_{subj}) + std(Amp_{pat}))}; SIa = \frac{1}{r}\sum SIa_r$$

One or more brain network activity pattern similarities S can then be calculated as a weighted average over the nodes of the brain network activity pattern, as follows:

$$Ss = \frac{\sum_i (W_i * SIs_i)}{\sum_i W_i}$$

$$Sa = \frac{\sum_i (W_i * SIa_i)}{\sum_i W_i}$$

$$Sf = \frac{\sum_i (W_i * SIf_i)}{\sum_i W_i}$$

$$Sl = \frac{\sum_i (W_i * SIl_i)}{\sum_i W_i}$$

Formally, an additional similarity, Sc, can be calculated, as follows:

$$Ic = \frac{\sum_i (W_i * SIc_i)}{\sum_i W_i},$$

where SIc$_i$ is a binary quantity which equals 1 if pair i exists in the subject's data and 0 otherwise.

In some applications of the present invention, the quantity SI includes a correlation value between recorded activities. For some applications, the correlation value describes correlation between the activities recorded for the specific subject at the two locations associated with the pair, and, for some applications, the correlation value describes correlation between the activities recorded for the specific subject at any of the locations associated with the pair and the group activities as recorded at the same location. For some applications, the correlation value describes causality relations between activities.

For some applications, procedures for calculating correlation values, such as causality relations that are known in the art, are used. For some applications, the Granger theory is employed (e.g., as described in Granger C W J, 1969, "Investigating Causal Relations By Econometric Models And Cross-Spectral Methods," Econometrica, 37(3):242, which is incorporated herein by reference). Other techniques suitable for the such applications are described in Durka et al., 2001, "Time-frequency microstructure of event-related electroencephalogram desynchronisation and synchronisation," Medical & Biological Engineering & Computing, 39:315; Smith Bassett et al., 2006, "Small-World Brain Networks" Neuroscientist, 12:512; He et al., 2007, "Small-World Anatomical Networks in the Human Brain Revealed by Cortical Thickness from MRI," Cerebral Cortex 17:2407; and De Vico Fallani et al., "Extracting Information from Cortical Connectivity Patterns Estimated from High Resolution EEG Recordings: A Theoretical Graph Approach," Brain Topogr 19:125; the contents of all of which are hereby incorporated by reference.

In accordance with respective applications, the connectivity weights assigned over the brain network activity pattern is calculated as a continuous variable (e.g., using a function having a continuous range), or as a discrete variable (e.g., using a function having a discrete range, or using a lookup table). Typically, connectivity weights can have more than two possible values. Thus, according to some applications of the present invention, the weighted brain network activity pattern has at least three, or at least four, or at least five, or at least six edges, each of which being assigned with a different connectivity weight.

Typically, once the brain network activity pattern is constructed it is transmitted to a display device such as monitor 18, or a printer (not shown). Alternatively or additionally, the brain network activity pattern is transmitted to a computer-readable medium.

For some applications, the subject-specific brain network activity pattern of a particular subject is compared to a previously constructed brain network activity pattern, e.g., the reference group brain network activity pattern constructed from EEG signals obtained from the subjects of the group on the first session based on a single pulse TMS-evoked potential (TEP). Optionally, a score is assigned to the subject-specific brain network activity pattern. Such a score can be, for example, a brain network activity pattern similarity score S. When the subject-specific brain network activity pattern is constructed based on the reference group brain network activity pattern (namely, when the subject-specific brain network activity pattern is a manifestation of the reference group brain network activity pattern, for the specific subject), the brain network activity pattern similarity S between the two brain network activity patterns is typically calculated based on the values of the connectivity weights of the subject-specific brain network activity pattern. For example, the brain network activity pattern similarity may be obtained by averaging the connectivity weights over the subject-specific brain network activity pattern.

When more than one type of connectivity weight is assigned for each pair of nodes in the subject-specific brain network activity pattern, the averaging is typically performed over the brain network activity pattern separately for each type of connectivity weight. Typically, one or more of the averages are combined (e.g., summed, multiplied, averaged, etc.) to provide a combined brain network activity pattern similarity. Alternatively, a representative of the averages (e.g., the largest) is defined as the brain network activity pattern similarity.

For some applications, the brain network activity pattern similarity is used as a score, which describes, quantitatively, the membership level of the subject to the group. Such a score is referred to as a brain network activity score. In the above-described example of a group brain network activity pattern constructed from EEG signals obtained on the first session based on a single pulse TEP, it describes the membership level (or lack of membership) of the subject to a group that is generally considered as a group of untreated subjects. Such applications are typically useful for determining the evolved effect of the TMS over the sessions for the subject.

For some applications, the brain network activity score is expressed as a continuous or discrete variable. Typically, the similarity is a non-binary number. In other words, rather than determining whether the two brain network activity patterns are similar or dissimilar, typically the degree by which the two brain network activity patterns are similar or dissimilar is calculated. For example, the similarity can be expressed as percentage, as a non-integer number between 0 and 1 (e.g., 0 corresponding to complete dissimilarity and 1 corresponding to comparison between a brain network activity pattern and itself), and the like.

Thus, for some applications of the present invention, at least one brain network activity pattern similarity is calculated, the similarity describing the similarity between the brain network activity pattern and a previously annotated brain network activity pattern.

EXAMPLES

Reference is now made to the following examples, which together with the above description illustrate some applications of the invention in a non-limiting fashion.

In experiments performed according to some applications of the present invention, dTMS treatment was administered in 20 stimulation sessions over a period of 4 weeks. The stimulation was performed over the left prefrontal cortex, at 10 Hz, and over the right prefrontal cortex, at 1 Hz. The 10 Hz stimulation was delivered using 2 second trains of 20 pulses with an inter train interval of 15 seconds, during which the 1 Hz stimulation was applied. EEG was recorded prior to start of treatment, then every 5 sessions (i.e., sessions 1, 6, and 11), and then on one of the days during the week after the last session. Each dTMS treatment included stimulation of 25.5 minutes of dual channel dTMS treatment.

The results described in this example were obtained from thirty healthy subjects and 24 major depressive disorder patients.

Figure 11A:
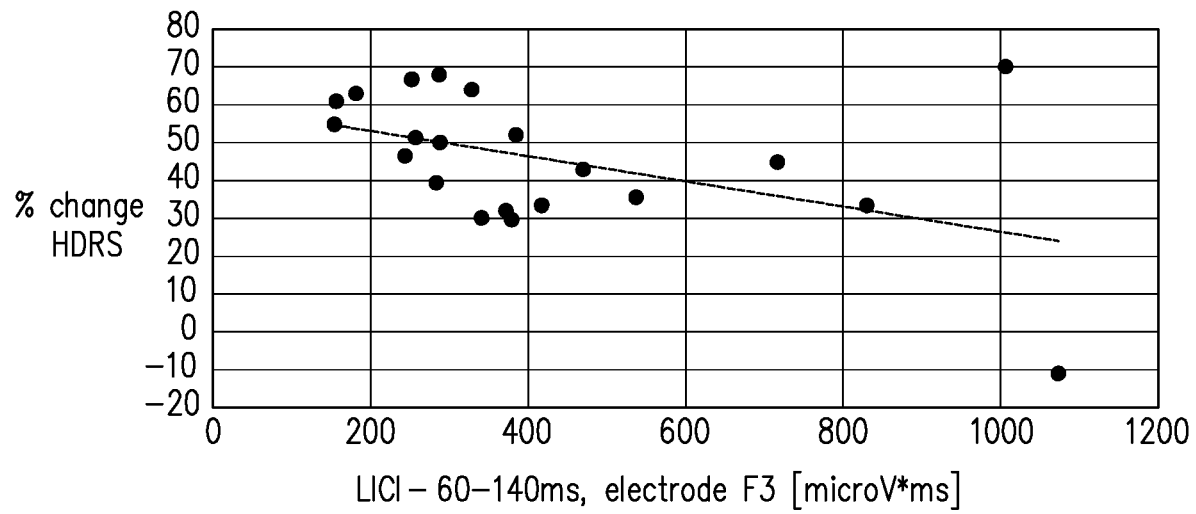
FIG. 11A is a graph indicating, for major depressive disorder patients to whom dTMS was applied, the degree of correlation between (a) improvements to patients' Hamilton depression rating scale ("HDRS") of major depressive disorder patients after four weeks of dTMS treatment versus (b) Long Interval Cortical Inhibition TMS-evoked potentials (LICI-TEP) deflection values corresponding to the difference between the single pulse and the second pulse in a pair that was recorded on the first day of a treatment prior to initiation of treatment, in accordance with some applications of the present invention.

Reference is now made to FIG. 11A, which is a graph indicating, for major depressive disorder patients to whom dTMS was applied, the degree of correlation between (a) improvements to patients' Hamilton depression rating scale ("HDRS") after four weeks of TMS treatment versus (b) Long Interval Cortical Inhibition TMS-evoked potentials (LICI-TEP) deflection values corresponding to the difference between the single pulse and the second pulse in a pair that was recorded on the first day of a treatment prior to initiation of treatment, in accordance with some applications of the present invention. The deflection values that are plotted on the x-axis of FIG. 11A are negativity deflection values of the difference waveform between the single pulse TEP and TEP of the second pulse in a pair (DIFF) recorded 60-140 after the TMS pulse at electrode F3, at the first treatment session prior to initiation of treatment. For the data shown in FIG. 11A, a 21-item questionnaire (HDRS-21) was used. The correlation coefficient is 0.473, the corresponding probability is 0.03.

According to the correlation in FIG. 11A, major depressive disorder patients with a smaller difference waveform as recorded prior to the initiation of dTMS treatment have a better chance of responding to dTMS treatment. Similar relationships can be obtained also for positive deflection values.

Figure 11B:
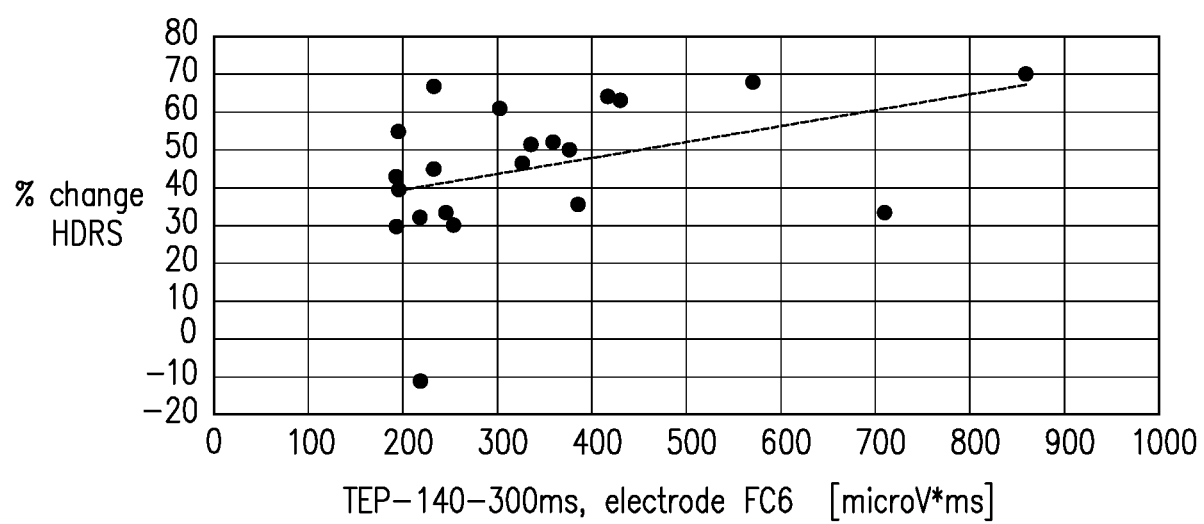
FIG. 11B is a graph indicating, for major depressive disorder patients to whom dTMS was applied, the degree of correlation between (a) improvements to patients' HDRS after four weeks of dTMS treatment versus (b) LICI-TEP deflection values generated by a single pulse that was recorded on the first day of a treatment prior to initiation of treatment, in accordance with some applications of the present invention.

Reference is now made to FIG. 11B, which is a graph indicating, for major depressive disorder patients to whom dTMS was applied, the degree of correlation between (a) improvements to patients' HDRS after four weeks of dTMS treatment versus (b) LICI-TEP deflection values generated by a single pulse that was recorded on the first day of a treatment prior to initiation of treatment, in accordance with some applications of the present invention. The deflection values that are plotted on the x-axis of FIG. 11B are single pulse TEP deflection values (area) recorded 140-300 ms after the TMS pulse at electrode FC6, at the first treatment session prior to initiation of treatment. For the data shown in FIG. 11B, a 21-item questionnaire (HDRS-21) was used. The correlation coefficient is 0.402, and the corresponding probability is 0.07.

According to the correlation in FIG. 11B, major depressive disorder patients with a larger TEP as recorded prior to the initiation of dTMS treatment have a better chance of responding to dTMS treatment.

Thirteen-second interval sections of the inter-treatment EEG signals were sampled, and the samples were spectrally analyzed, such that the powers of respective frequency components within the samples were calculated. At the end of the treatments, the patients' HDRS were measured in order to measure the responsiveness of the patients to the dTMS treatments. The responsiveness of the patients to the treatment was then compared to the power of the respective frequency components of the thirteen-second interval EEG samples as recorded at the first treatment session, prior to the initiation of treatment.

Figure 12A:
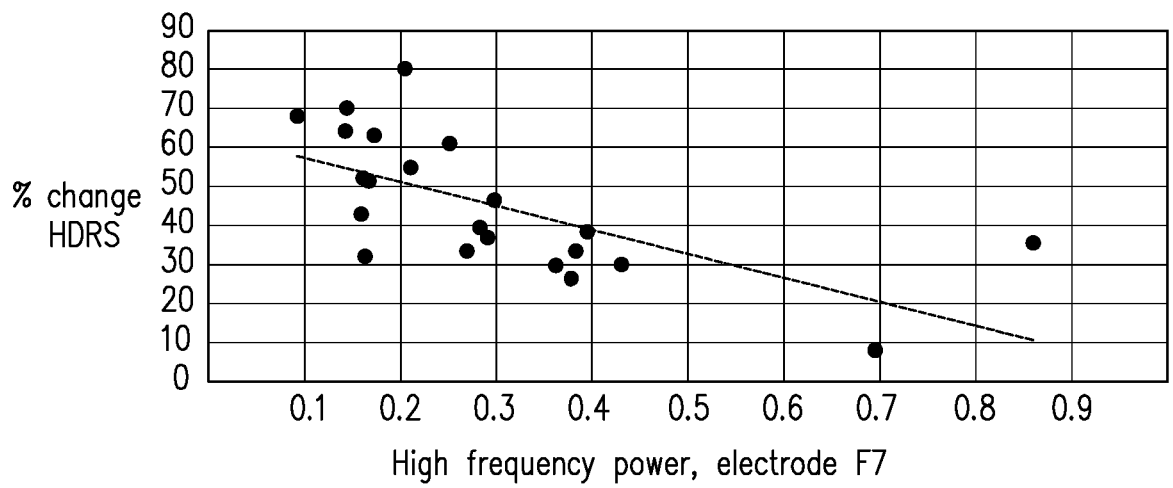
FIGS. 12A and 12B are graphs indicating, for major depressive disorder patients to whom dTMS was applied, the degree of correlation between (a) improvements to patients' HDRS measure after four weeks of TMS treatment, versus (b) the power of respective frequency components of thirteen-second interval EEG samples as recorded at the indicated EEG electrode at the first treatment session prior to initiation of treatment, FIG. 12A corresponding to a high-frequency wave (20-40 Hz) at electrode location F7, and FIG. 12B corresponding to a Low Gamma wave (30-40 Hz) at electrode location F7, in accordance with some applications of the present invention.
Figure 12B:
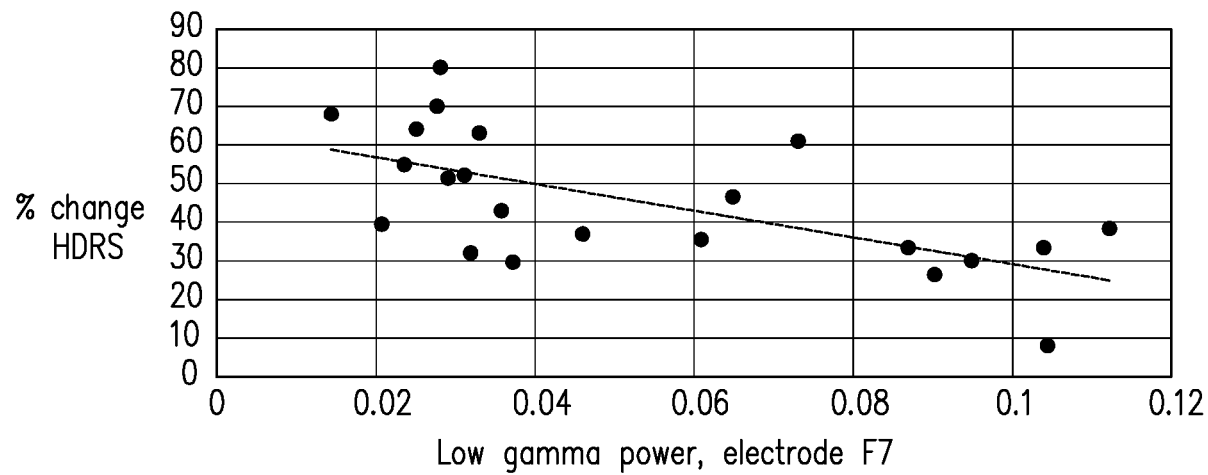

Reference is now made to FIGS. 12A and 12B, which are graphs indicating, for major depressive disorder patients to whom dTMS was applied, the degree of correlation between (a) improvements to patients' HDRS measure after four weeks of TMS treatment, versus (b) the power of respective frequency components of thirteen-second interval EEG samples, as recorded at electrode location F7, at the first treatment session prior to initiation of treatment, FIG. 12A corresponding to a high-frequency wave (20-40 Hz) at electrode location F7, and FIG. 12B corresponding to a Low Gamma wave (30-40 Hz) at electrode location F7, in accordance with some applications of the present invention. As shown, there is a correlation between both of the frequency components of the thirteen-second interval EEG samples as recorded at the first treatment session, and the improvements to the patients' HDRS. The correlation is negative in the high frequency range (20-40 Hz) at electrode F7 (with a correlation coefficient of −0.65), meaning that patients with lower left frontal high frequency power at the beginning of the TMS treatment showed greater responsiveness to the treatment. The correlation was also negative in the low gamma range (30-40 Hz) at electrode F7 (with a correlation value of −0.64), meaning that patients with lower left frontal gamma power at the beginning of the TMS treatment showed greater responsiveness to the treatment. Both correlations were statistically significant (with a probability of less than 0.001 for the data shown in each of FIGS. 12A and 12B).

It is noted that although the EEG signals from which the samples were taken and spectrally analyzed were recorded at the first treatment session of a four-week course of treatment, the graphs shown in FIGS. 12A-B indicates that there is a correlation between the power of certain frequency components of the sample and the responsiveness of the patients to the treatment, as measured after the four-week course of treatment.

Respective group brain network activity patterns were constructed from EEG signals acquired after TMS pulses (single, paired) were applied to both the healthy subjects and the major depressive disorder patients. In addition, subject-specific brain network activity patterns were constructed, and brain network activity similarity scores of the subject-specific brain network activity patterns were calculated.

Figure 13A:
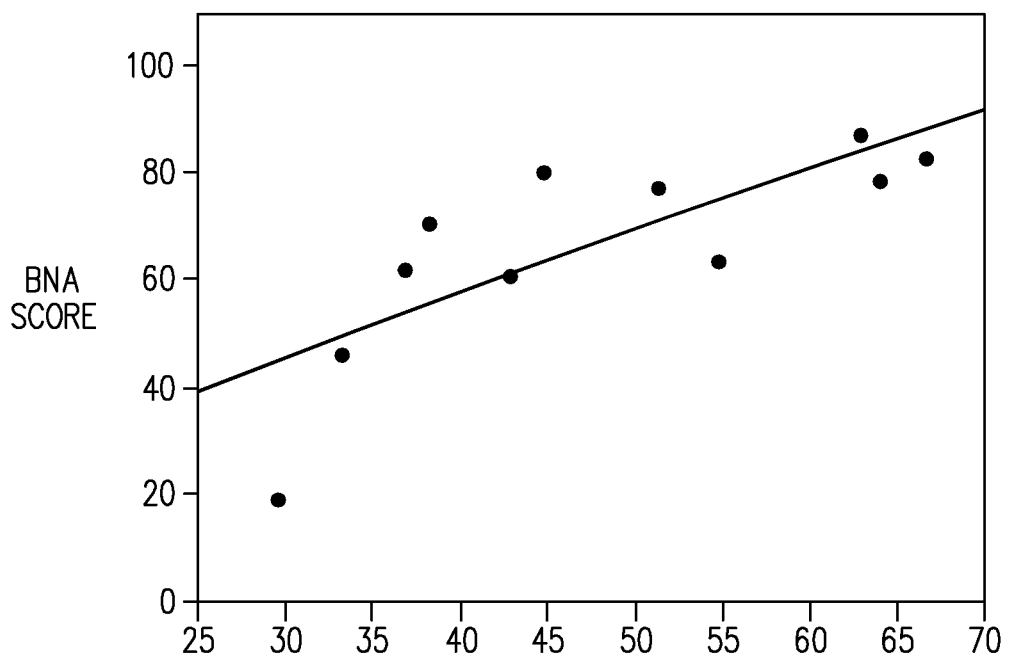
FIG. 13A is a graph showing the relationship between (a) the percentage improvement to major depressive disorder patients' HDRS after three weeks of treatment versus (b) the patients' brain network activity similarity scores generated by single pulse TEP as recorded prior to treatment commencing and as compared to the brain network activity of healthy subjects, in accordance with some applications of the present invention.

FIG. 13A is a graph showing the relationship between (a) the percentage improvement to major depressive disorder patients' HDRS after three weeks of treatment versus (b) the patients' brain network activity similarity scores generated by single pulse TEP as recorded prior to treatment commencing, and as compared to the brain network activity of healthy subjects, in accordance with some applications of the present invention The correlation coefficient is 0.775268, the corresponding probability is 0.0051 and the number of subjects is 11. For the data shown in FIG. 13A, a 21-item questionnaire (HDRS-21) was used. The graph demonstrates that patients that obtained high brain network activity similarity scores with respect to the healthy subjects, showed the greatest benefit from the dTMS treatment, and that the brain network activity score successfully predicts the responsiveness of major depressive disorder patients to dTMS treatment. Similar correlations were obtained using a reference group brain network activity pattern constructed from EEG signals obtained after the second pulse in a paired-pulse TMS stimulation, demonstrating that predicting TMS treatment responsiveness based brain network activity is not limited to just one type of TMS pulse.

Figure 13B:
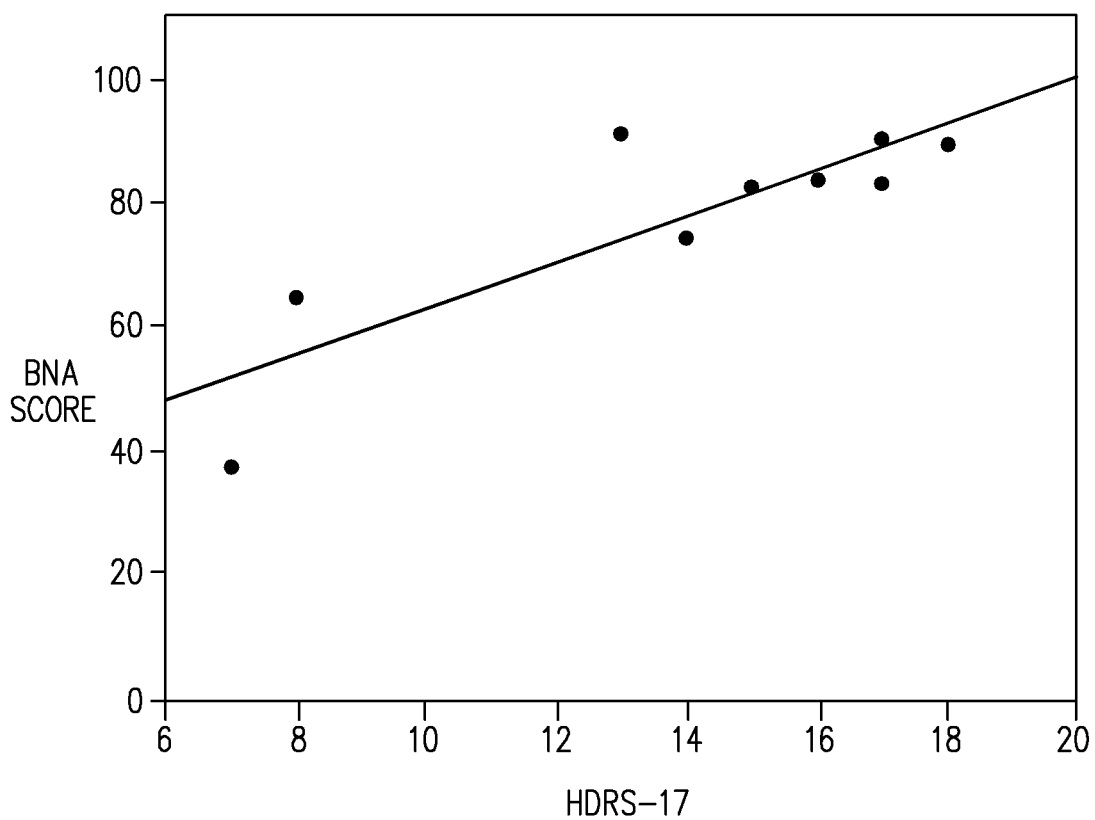
FIG. 13B is a graph showing the relationship between (a) similarity scores of the brain network activity of major depressive disorder patients generated by single pulse TEP, as compared to the brain network activity of major depressive disorder patients, and (b) the patients' HDRS, in accordance with some applications of the present invention.

Reference is also made to FIG. 13B, which is a graph showing the relationship between (a) similarity scores of the brain network activity of major depressive disorder patients generated by single pulse TEP, as compared to the brain network activity of major depressive disorder patients, and (b) the patients' HDRS, in accordance with some applications of the present invention. The correlation coefficient of the data shown in FIG. 13B is 0.853554, the corresponding probability is 0.0017. For the data shown in FIG. 13B, a 17-item questionnaire (HDRS-17) was used.

The similarity scores were generated based upon brain network activity patterns of the patients that were generated after three weeks of treatment, and the HDRS of the patients were also measured at the same point in time. As indicated by the relationship shown in FIG. 13B, at a given moment in time, there is a correlation between the similarity scores of the brain network activity of the patients, as compared to the brain network activity of major depressive disorder patients, and the patients' HDRS. The data shown in FIG. 13B indicate that the brain network activity of patients suffering from a given neuropsychiatric condition can be used to measure the severity of their condition as an alternative to, or in addition to, their condition being graded by used of standard models. For example, based on the data shown in FIG. 13B, as an alternative to, or in addition to, using HDRS questionnaires to grade major depressive disorder patients (which is typically a time-consuming procedure), the patients' brain network activity can be measured and the patients can be graded based upon their brain network activity (e.g., by comparing their brain network activity to that of a group of healthy subjects, or to that of a group of unhealthy subjects).

Figure 14A:
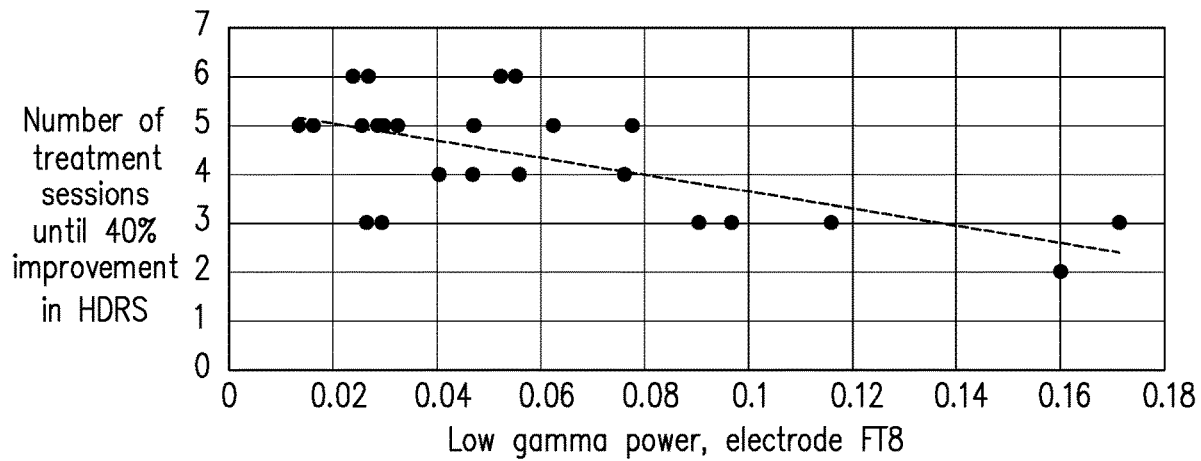
FIGS. 14A and 14B are graphs showing the relationship between (a) the time after initiating dTMS treatment of major depressive disorder patients to respective percentage improvements from pre-treatment baseline in the patients' HDRS, and (b) the power of respective frequency components of the thirteen-second interval EEG samples as recorded at respective EEG electrodes prior to treatment commencing, in accordance with some applications of the present invention.
Figure 14B:
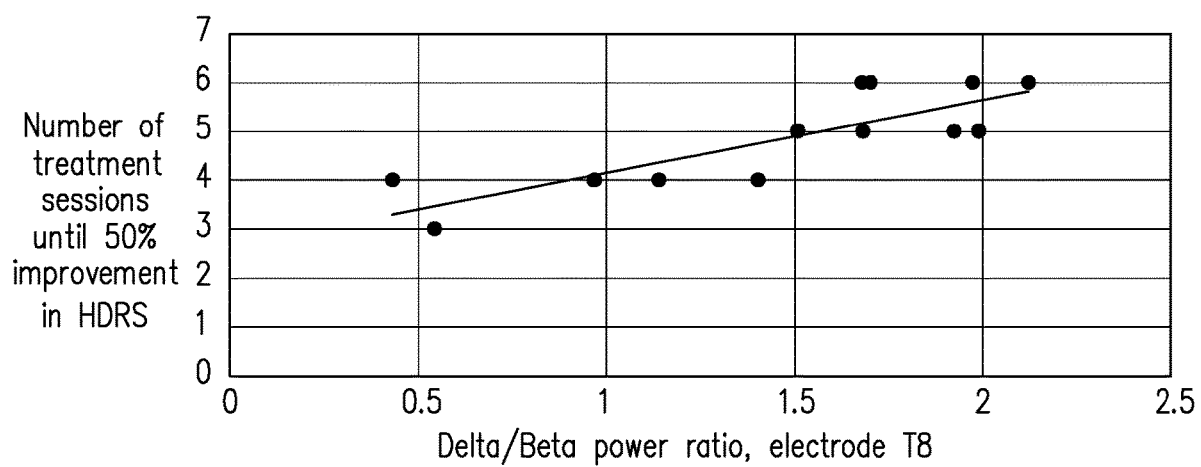

Reference is now made to FIGS. 14A and 14B, which are graphs showing the relationship between (a) the time after initiating dTMS treatment of major depressive disorder patients to respective percentage improvements from pre-treatment baseline in the patients' HDRS, and (b) the power of respective frequency components of the thirteen-second interval EEG samples as recorded at respective EEG electrodes prior to treatment commencing, in accordance with some applications of the present invention. Specifically, FIG. 14A plots the number of EEG visits until the patients reached a 40 percent improvement in their HDRS relative to their pre-treatment HDRS, against the low gamma power (30-40 Hz) recorded at electrode FT8 in response to a TMS pulse that was applied on the first day of treatment, prior to commencement of treatment. The correlation between the time taken to the 40 percent HDRS improvement relative to the low gamma power was negative, with a correlation value of −0.63, indicating that patients with lower right fronto-lateral low gamma power prior TMS treatment showed a slower response to the treatment.

FIG. 14B plots the number of EEG until the patients reached a 50 percent improvement in their HDRS relative to their pre-treatment HDRS, against the delta (1-4 Hz) to beta (12-30 Hz) power ratio as recorded at electrode T8 in response to a TMS pulse that was applied on the first day of treatment, prior to commencement of treatment. The correlation between the time taken to the 50 percent HDRS improvement relative to the delta-to-beta power ratio was positive, with a correlation value of 0.83, indicating that patients with lower right lateral delta-to-beta power ratio at the prior to TMS treatment showed faster response to the treatment. The correlations demonstrated in both FIG. 14A and FIG. 14B are statistically significant (p<0.001).

In accordance with the results shown in FIGS. 14A and 14B, the EEG power spectral density function obtained prior to treatment commencing, is highly correlated with the time to response to treatment, as measured using HDRS. Therefore, in accordance with some applications of the present invention, even prior to treatment of a subject commencing, one or more pulses of transcranial magnetic stimulation are applied to the subject. Within a given time period of applying one of the one or more pulses of transcranial magnetic stimulation to the subject, an electrophysiological signal of the subject (e.g., the subject's EEG) is detected. At least partially in response to the detected electrophysiological signal, the time that it will take to treat (or at least partially treat) the subject for a neuropsychiatric condition, using a given therapy, is predicted. Alternatively or additionally, a rate of the improvement in the subject's condition, in response to the treatment, is predicted. For some applications, the power density of specific frequency bands is measured, and the prediction is made responsively thereto. Alternatively or additionally, a relationship (e.g., a ratio) between the power densities of two or more frequency bands is detected, and the prediction is made responsively thereto.

Reference is now made to FIGS. 15A, 15B, and 15C are flowcharts showing steps that are performed by a computer processor, in accordance with some applications of the present invention.

As shown in FIG. 15A, and in accordance with the above description, for some applications in step 40, the computer processor drives TMS device 10 (FIG. 1) to apply one or more TMS pulses to a subject suffering from a given neuropsychiatric condition. In step 42, the computer processor detects an electrophysiological signal of the subject signal subsequent to the one or more pulses being applied. For example, the subject's EEG may be detected using electrodes 14 (shown in FIG. 1). For some applications, the EEG recorded at one or more given electrodes is detected. In step 44, the computer processor predicts the outcome of treating the subject using a given treatment, responsively to the detected electrophysiological signal. In accordance with the data shown in FIGS. 14A and 14B, for some applications, as part of step 44, the computer processor predicts the time that it will take until the subject's condition improves by a given amount, and/or predicts a rate of the improvement in the subject's condition, in response to the given treatment being applied to the subject.

The flowchart shown in FIG. 15B is generally similar to that of FIG. 15A. However, the flowchart shown in 15B, includes additional steps 46 and 48, in accordance with some applications of the present invention. For some applications, the power density of one or more given frequency bands within the detected electrophysiological signal is measured, as indicated in step 46. In step 48 (which is optional, as indicated by the dashed box), the power densities of two or more frequency bands are combined. Typically, a relationship (e.g., a ratio) between the power densities of the two or more frequency bands is calculated. For some applications, step 44 (in which the subject's response to treatment using a given therapy is predicted) is performed in response to step 46, and/or step 48.

The flowchart shown in FIG. 15C is generally similar to that of FIG. 15A. However, the flowchart shown in 15B, includes additional steps 50 and 52, in accordance with some applications of the present invention. For some applications, in step 50, the subject's brain network activity pattern is constructed based on the detected electrophysiological signal, e.g., using techniques described hereinabove. For some applications, in step 52 (which is optional, as indicated by the dashed box), a similarity score is calculated for the subject's brain network activity patter, e.g., by comparing the subject's brain network activity pattern to a group pattern, such as a healthy subject group pattern, or the pattern of a group suffering from a given neuropsychiatric condition. For some applications, step 44 (in which the subject's response to treatment using a given therapy is predicted) is performed in response to step 50, and/or step 52.

Although some applications have been described herein according to which a train of pulses of TMS is applied to a subject, the scope of the present invention includes using an electrophysiological response to a single pulse of TMS for predicting a subject's response to a treatment, in accordance with the general techniques described herein, mutatis mutandis. Although some applications have been described herein, according to which a subject's EEG signal is measured at a given time after a TMS pulse train has been applied, the scope of the present invention includes using an electrophysiological response that is measured at various time points following a given transcranial magnetic stimulation pulse for predicting a subject's response to a treatment, in accordance with the general techniques described herein, mutatis mutandis. For example, when a TMS protocol is applied using a given set of train and inter-train intervals, EEG recordings (or other electrophysiological recordings) may be measured at any of the following times:

1. A given time period after one of the TMS pulses, e.g., a time period that is more than 1 ms, and/or less than 10 ms (e.g., between 1 ms and 10 ms) after the application of the pulse, or a time period that is more than 10 ms, and/or less than 100 ms (e.g., between 10 ms and 100 ms) after the application of the pulse, or a time period that is more than 100 ms, and/or less than 1 second (e.g., between 100 ms and 1 second) after the application of the pulse.

2. Within a given train, in between successive TMS pulses.

3. During inter-train intervals, for example, more than 1 second, and/or less than 20 seconds (e.g., between 1 second and 20 seconds) after the application of a train.

For some applications, a plurality of electrophysiological measurements that were recorded at respective times with respect to application of TMS, are averaged (or otherwise combined) over several minutes or over a full TMS session, and the subject's response to a treatment is predicted responsively thereto, in accordance with the general techniques described herein, mutatis mutandis.

Generally, the scope of the present invention includes using any form of TMS configuration (e.g., using dTMS coils, or TMS using figure-eight coils) and any form of stimulation protocol (e.g. including single pulses, paired pulses, single trains and multiple trains), and predicting the responsiveness of the patient to various kinds of treatment, including TMS treatment, dTMS treatment, pharmacological treatment, behavioral or psychotherapy treatment, deep brain stimulation (DBS) treatment, electroconvulsive therapy (ECT) treatment and other treatments, based upon a component of an electrophysiological signal of the patient (e.g., the patient's EEG) recorded during or subsequent to TMS being applied to the patient.

Moreover, for some applications, the analysis of a component of the patient's electrophysiological signal recorded subsequent to the application of a TMS pulse (or train, or trains of pulses) is combined with the patient's electrophysiological signal during a certain task, and the combined neuromarker (e.g. a ratio or any other mathematical combination) is used as a predictor for response to treatment. In addition to the use of electrophysiological recordings for prediction of response to treatment, electrophysiological recordings as described in the present invention may be used for diagnosis, for disease characterization, for assessment of disease severity and/or for discrimination between healthy subjects and subjects suffering from a neuropsychiatric disorder.

The inventors of the present application hypothesize that similar effects to the above-described effects which were observed for ADHD patients and major depressive disorder patients would be evident for patients suffering from other conditions, such as depression and other neuropsychiatric disorders such as bipolar disorder, autism, post-traumatic stress disorder (PTSD), addictive behaviors (including smoking, overeating and drug addiction), schizophrenia, Parkinson's disease, Alzheimer's disease, obsessive compulsive disorder (OCD), epilepsy, and others. Therefore, the scope of the present invention includes applying the apparatus and methods described herein to patients suffering from any one of the aforementioned conditions, mutatis mutandis.

It is noted that the terms "patient" and "subject" are used interchangeably in the present application.

Applications of the invention described herein can take the form of a computer program product accessible from a computer-usable or computer-readable medium (e.g., a non-transitory computer-readable medium) providing program code for use by or in connection with a computer or any instruction execution system. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage is used.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that the techniques described herein, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowcharts and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the algorithms described herein. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the algorithms described in the present application.

Computer processors described herein are typically hardware devices programmed with computer program instructions to produce a special purpose computer. For example, when programmed to perform the algorithms described herein, the computer processor typically acts as a special purpose treatment-outcome-prediction computer processor. Typically, the operations described herein that are performed by computer processors transform the physical state of a memory, which is a real physical article, to have a different magnetic polarity, electrical charge, or the like depending on the technology of the memory that is used.

The scope of some embodiments of the present invention includes combining methods and apparatus described in any one of the following patent applications, with those described in the present application:

WO 14/128631 to Zangen;
WO 14/128632 to Zangen;
WO 14/128630 to Zangen;
WO 13/121359 to Pell;
WO 06/134598 to Zangen;
US 2014/0249352 to Zangen;
US 2014/0235928 to Zangen;
US 2014/0235927 to Zangen;
US 2014/0235926 to Zangen;
US 20130178692 to Zangen; and WO 2011/086563 to Shahaf.

Each of the above-referenced applications is incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with electrophysiological signal detecting electrodes, and a transcranial magnetic stimulation device, the apparatus comprising:
    an output device; and
    a computer processor configured to:
        drive the transcranial stimulation device to apply one or more pulses of transcranial magnetic stimulation to a subject by driving the transcranial stimulation device to apply a plurality of trains of transcranial magnetic stimulation to the subject;
        detect an electrophysiological signal of the subject using the electrophysiological signal detecting electrodes within a given time period of applying one of the one or more pulses of transcranial magnetic stimulation to the subject, wherein the given time period occurs between successive pulses of a given train of transcranial magnetic stimulation;
        at least partially in response to the electrophysiological signal detected within the given time period, predict an outcome of treating the subject for a neuropsychiatric condition, using a given therapy; and
        generate an output on the output device in response to the predicted outcome.

2. The apparatus according to claim 1, wherein the computer processor is configured to predict the outcome of treating the subject for the neuropsychiatric condition, using the given therapy, by predicting an outcome of treating the subject for depression using transcranial magnetic stimulation.

3. The apparatus according to claim 1, wherein the computer processor is configured to predict the outcome of treating the subject for the neuropsychiatric condition, using the given therapy, by predicting an outcome of treating the subject for ADHD using transcranial magnetic stimulation.

4. The apparatus according to claim 1, wherein the computer processor is configured to detect the electrophysiological signal of the subject by detecting an electroencephalography signal of the subject.

5. The apparatus according to claim 1, wherein the computer processor is configured to predict the outcome of treating the subject for the neuropsychiatric condition using the given therapy by predicting a response time of the subject to being treated with the given therapy.

6. The apparatus according to claim 1, wherein the computer processor is configured to predict the outcome of treating the subject for the neuropsychiatric condition using the given therapy by predicting a rate of improvement in the subject's neuropsychiatric condition, in response to being treated with the given therapy.

7. The apparatus according to claim 1, wherein:
    the computer processor is further configured to detect an electroencephalography (EEG) signal of the subject while the subject performs a task, and
    the computer processor is configured to predict the outcome of treating the subject for the neuropsychiatric condition using the given therapy, based upon the electrophysiological signal of the subject and a component of the EEG signal of the subject that was detected while the subject performed the task.

8. The apparatus according to claim 1, wherein the computer processor is further configured to construct a brain network activity pattern based on the electrophysiological signal, and the computer processor is configured to predict the outcome of treating the subject for the neuropsychiatric condition using the given therapy based on the brain network activity pattern.

9. The apparatus according to claim 8, wherein the computer processor is further configured to calculate a brain network activity pattern similarity score, by comparing the brain network activity pattern to a group brain network activity pattern that is based upon electrophysiological signals acquired from a group of subjects, and the computer processor is configured to predict the outcome of treating the subject for the neuropsychiatric condition using the given therapy based on the brain network activity pattern similarity score.

10. The apparatus according to claim 8, wherein:
    the computer processor is configured to construct the brain network activity pattern by constructing a brain network activity pattern using reference neurophysiological data, the reference neurophysiological data being electrophysiological signals acquired from a group of subjects, each applied with an initial pulse of transcranial magnetic stimulation.

11. The apparatus according to claim 8, wherein:
    (A) the computer processor is configured to construct the brain network activity pattern by constructing a brain network activity pattern that includes:
        a plurality of nodes, each representing a comparison of features and relations among features in the electrophysiological signal to features and relations among features of reference neurophysiological data; and
        connectivity weights assigned to respective pairs of nodes, and
    (B) the computer processor is configured to construct the brain network activity pattern by constructing a brain network activity pattern in which each node represents a cluster of vectors of data characteristics, and the connectivity weights of each one of the respective nodes represents at least one cluster property describing a pair of clusters represented by said the respective pair of nodes.

12. The apparatus according to claim 1, wherein the computer processor is further configured to calculate a power of a given frequency band within the detected electrophysiological signal, and the computer processor is configured to predict the outcome of treating the subject for the neuropsychiatric condition using the given therapy at least partially in response to the power of the given frequency band.

13. The apparatus according to claim 12, wherein:
    the computer processor is further configured to calculate powers of one or more additional frequency bands within the detected electrophysiological signal, and
    the computer processor is configured to predict the outcome of treating the subject for the neuropsychiatric condition using the given therapy, based upon a combination of the power of the given frequency band and the powers of the one or more additional frequency bands.

14. The apparatus according to claim 13, wherein the computer processor is configured to predict the outcome of treating the subject for the neuropsychiatric condition using the given therapy, based upon a ratio of the power of the given frequency band and the power of one of the one or more additional frequency bands.

15. The apparatus according to claim 12, wherein the computer processor is configured to detect the electrophysiological signal of the subject by detecting an electroencephalography signal of the subject.

16. The apparatus according to claim 15, wherein the computer processor is configured to calculate the power of the given frequency band within the detected electrophysiological signal by calculating a power of a low gamma band within the detected electroencephalography signal.

17. The apparatus according to claim 16, wherein:
the computer processor is further configured to calculate a power of an alpha band within the detected electroencephalography signal, and
the computer processor is configured to predict the outcome of treating the subject for the neuropsychiatric condition using the given therapy, based upon a combination of the power of the low gamma band within the detected electroencephalography signal and the power of the alpha band within the detected electroencephalography signal.

18. The apparatus according to claim 1, wherein the given time period is within 1-1000 ms of the applying of the one of the one or more pulses of transcranial magnetic stimulation to the subject, and the computer processor is configured to predict the outcome of treating the subject for a neuropsychiatric condition, using the given therapy, at least partially in response to the electrophysiological signal detected within 1-1000 ms of the applying of the one of the one or more pulses of transcranial magnetic stimulation to the subject, within a given train, in between successive pulses of transcranial magnetic stimulation.

19. A computer software product, for use with an output device, electrophysiological signal detecting electrodes, and a transcranial magnetic stimulation device, the computer software product comprising a non-transitory computer-readable medium in which program instructions are stored, which instructions, when read by a computer cause the computer to perform the steps of:
driving the transcranial stimulation device to apply one or more pulses of transcranial magnetic stimulation to a subject by driving the transcranial stimulation device to apply a plurality of trains of transcranial magnetic stimulation to the subject;
detecting an electrophysiological signal of the subject using the electrophysiological signal detecting electrodes within a given time period of applying one of the one or more pulses of transcranial magnetic stimulation to the subject, wherein the given time period occurs between successive pulses of a given train of transcranial magnetic stimulation;
at least partially in response to the electrophysiological signal detected within the given time period, predicting an outcome of treating the subject for a neuropsychiatric condition, using a given therapy; and
generating an output on the output device in response to the predicted outcome.

20. A method comprising:
applying one or more pulses of transcranial magnetic stimulation to a subject by driving a transcranial stimulation device to apply a plurality of trains of transcranial magnetic stimulation to the subject;
detecting an electrophysiological signal of the subject within a given time period of applying one of the one or more pulses of transcranial magnetic stimulation to the subject, wherein the given time period occurs between successive pulses of a given train of transcranial magnetic stimulation; and
at least partially in response to the electrophysiological signal detected within the given time period, predicting an outcome of treating the subject for a neuropsychiatric condition, using a given therapy.

21. The method according to claim 20, wherein the given time period is within 1-1000 ms of the applying of the one of the one or more pulses of transcranial magnetic stimulation to the subject, and predicting the outcome of treating the subject for a neuropsychiatric condition, using the given therapy, comprises predicting the outcome of treating the subject for a neuropsychiatric condition, using the given therapy, at least partially in response to the electrophysiological signal detected within 1-1000 ms of the applying of the one of the one or more pulses of transcranial magnetic stimulation to the subject, within a given train, in between successive pulses of transcranial magnetic stimulation.

* * * * *

UNITED STATES PATENT AND TRADEMARK OFFICE
CERTIFICATE OF CORRECTION

| | |
|---|---|
| PATENT NO. | : 11,400,289 B2 |
| APPLICATION NO. | : 16/344499 |
| DATED | : August 2, 2022 |
| INVENTOR(S) | : Uri Alyagon et al. |

It is certified that error appears in the above-identified patent and that said Letters Patent is hereby corrected as shown below:

In the Claims

At Column 29, Claim number 1, Line numbers 33-35, replace:
"chiatric condition, using a given therapy; and
generate an output on the output device in response to
the predicted outcome."

With:
--chiatric condition, using a given therapy;
generate an output on the output device in response to
the predicted outcome, and perform the given
therapy based on the predicted outcome.--

At Column 32, Claim number 19, Line numbers 14-16, replace:
"atric condition, using a given therapy; and
generating an output on the output device in response to
    the predicted outcome."

With:
--atric condition, using a given therapy;
generating an output on the output device in response to
    the predicted outcome, and perform the given therapy
based on the predicted outcome.--

At Column 32, Claim number 20, Line number 27, replace:
"nial magnetic stimulation; and"

With:
--nial magnetic stimulation;--

Signed and Sealed this
Thirteenth Day of December, 2022

*Katherine Kelly Vidal*
Katherine Kelly Vidal
*Director of the United States Patent and Trademark Office*

At Column 32, Claim number 20, Line number 31, replace:
"atric condition, using a given therapy."

With:
--atric condition, using a given therapy, and performing the given therapy based on the predicted outcome.--